United States Patent [19]
Gold et al.

[11] Patent Number: 5,843,701
[45] Date of Patent: Dec. 1, 1998

[54] SYSTEMATIC POLYPEPTIDE EVOLUTION BY REVERSE TRANSLATION

[75] Inventors: Larry Gold; Craig Tuerk, both of Boulder, Colo.; David Pribnow, Portland, Oreg.; Jonathan Drew Smith, Boulder, Colo.

[73] Assignee: NeXstar Pharmaceticals, Inc., Boulder, Colo.

[21] Appl. No.: 829,461

[22] Filed: Jan. 31, 1992

Related U.S. Application Data

[63] Continuation-in-part of Ser. No. 739,055, Aug. 1, 1991, abandoned, and a continuation-in-part of Ser. No. 561,968, Aug. 2, 1990, abandoned.

[51] Int. Cl.[6] .............................. C12P 21/02; C12N 15/00
[52] U.S. Cl. ..................... 435/68.1; 435/691; 435/172.1; 435/172.3; 935/3; 935/4; 935/10; 935/17
[58] Field of Search .................................. 435/435, 68.1, 435/69.1, 69.2, 69.3, 69.4, 69.5, 69.6; 935/3, 4, 10, 11, 12, 13, 14, 15, 16, 17, 21, 44

[56] References Cited

U.S. PATENT DOCUMENTS 5,658,754  8/1997  Kawasaki et al. ..................... 435/68.1

FOREIGN PATENT DOCUMENTS

| 2 183 661 A | 6/1987 | United Kingdom . |
|---|---|---|
| WO89/06694 | 7/1989 | WIPO . |
| WO92/14843 | 9/1992 | WIPO . |

OTHER PUBLICATIONS

Krisch et al. Nucleotide sequences involved in bacteriophage T4 gene 32 translational self regulation. Proc. Nat. cad. Sci. USA 79:4937–4941, Aug. 1982.

Formosa et al. Affinity purification of bacteriophage T4 proteins essential for DNA replication ad genetic recombination. Proc. Nat. Acad. Sci., USA 80: 2442–2446, May 1983.

Krassa et al. Protein–protei interactions with the acidic COOH terminus of the single stranded DnA binding protein of the bacteriophage T4, May 1991.

Joyce (1989) Gene 82:83.

Joyce & Inoue (1989) Nucleic Acids Research 17:711.

Ellington & Szostak (1990) Abstracts of papers presented at the 1990 meeting on RNA Processing, Cold Spring Harbor Laboratory, Cold Spring Harbor, NY, p. 84.

Kinzler & Vogelstein (1989) Nucleic Acids Research 17:3645.

Kramer et al. (1974) J. Mol. Biol. 89:719.

Levisohn & Spiegelman (1969) PNAS USA 63:805.

Levisohn & Spiegelman (1968) PNAS USA 60–866.

Oliphant et al. (1989) Mol. Cell. Biol. 9:2944.

Oliphant & Struhl (1988) Nucleic Acids Reseach 16:7673.

Oliphant & Struhl (1987) Methods in Enzymology 155:568.

Oliphant et al. (1986) Gene 44:177.

Robertson & Joyce (1990) Nature 344:467.

Thiesen & Bach (1990) Nucleic Acids Research 18:3203.

*Primary Examiner*—Robert A. Wax
*Assistant Examiner*—Gabriele E. Bugaisky
*Attorney, Agent, or Firm*—Swanson & Bratschun LLC

[57] ABSTRACT

A method for preparing polypeptide ligands of target molecules wherein candidate mixtures comprised of ribosome complexes or mRNA·polypeptide copolymers are partitioned relative to their affinity to the target and amplified to create a new candidate mixture enriched in ribosome complexes or mRNA·polypeptide copolymers with an affinity to the target.

40 Claims, 8 Drawing Sheets

SYSTEMATIC POLYPEPTIDE EVOLUTION BY REVERSE TRANSLATION

CROSS REFERENCE TO RELATED APPLICATIONS

This application is a continuation-in-part of U.S. patent application Ser. No. 07/739,055, filed Aug. 1, 1991 now abandoned and U.S. patent application Ser. No. 07/561,968, filed Aug. 2, 1990, now abandoned both of which are entitled Systematic Polypeptide Evolution by Reverse Translation.

This work was supported by grants from the United States Government funded through the National Institutes of Health. The U.S. Government has certain rights in this invention.

FIELD OF THE INVENTION

We describe herein novel high-affinity polypeptide ligands that specifically bind a desired target molecule. A method is presented for selecting a polypeptide ligand that specifically binds any desired target molecule. The method is termed SPERT, an acronym for Systematic Polypeptide Evolution by Reverse Translation. The method of the invention (SPERT) is useful to isolate a polypeptide ligand for a desired target molecule. The polypeptide products of the invention are useful for any purpose to which a binding reaction may be put, for example in assay methods, diagnostic procedures, cell sorting, as inhibitors of target molecule function, as probes, as sequestering agents and the like. In addition, polypeptide products of the invention can have catalytic activity. Target molecules include natural and synthetic polymers, including proteins, polysaccharides, glycoproteins, hormones, receptors and cell surfaces, nucleic acids, and small molecules such as drugs, metabolites, cofactors, transition state analogs and toxins.

BACKGROUND OF THE INVENTION

As translation of mRNA proceeds, stable complexes are formed. These complexes are made of ribosomes bound to mRNA with tRNA and nascent polypeptide encoded by the messenger RNA. Termed "ribosome complexes" herein, such complexes can be isolated by various known processes (Connolly and Gilmore (1986) J. Cell Biol. 103:2253; Perara et al. (1986) Science 232:348). Antigen-encoding mRNAs have been purified by taking advantage of the immunoreactivity of nascent polypeptides associated with ribosome complexes (Sambrook, J., Fritsch, E. F., Maniatis, T. *Molecular Cloning: A Laboratory Manual* (Cold Spring Harbor, N.Y.) (1989) ibid. sections 8.9–8.10). Such immunoreactive ribosome complexes can be immunoprecipitated from solution or separated by protein A column chromatography from non-reactive ribosome complexes (Schutz et al. (1977) Nuc. Acids Res. 4, 71; Shapiro and Young (1981) J. Biol. Chem. 256, 1495). Cyclical selection and amplification of RNAs with partitionable properties is now also possible. Historically, mRNA selection is closely tied to immunopurification of ribosome complexes, however, the partitioning of ribosome complexes according to the present invention is not restricted to immunoreactivity of the nascent polypeptides.

SUMMARY OF THE INVENTION

In its broadest aspect, the method of systematic polypeptide evolution by reverse translation (SPERT) includes a candidate mixture of polypeptides having a randomized amino acid sequence. Each member of the mixture is linked to an individualized mRNA which encodes the amino acid sequence of that polypeptide. The candidate polypeptides are partitioned according to their property of binding to a given desired target molecule. The partitioning is carried out in such a way, herein described, that each mRNA encoding a polypeptide is partitioned exactly together with that polypeptide. In this way each polypeptide is partitioned together with the means for further amplifying it by an in vitro process. Ultimately, both the desired optimal polypeptide ligand of the desired target and the mRNA encoding the polypeptide are simultaneously selected, allowing further synthesis of the selected polypeptide as desired, and further amplification of the coding sequence. It is therefore not necessary to analyze the amino acid sequence of the selected polypeptide (using protein chemistry) in order to produce it in desired quantities.

Viewed another way, the invention is the selective evolution of a nucleic acid that encodes a polypeptide ligand of a desired target. The present method is therefore a selection based upon coding properties available in a candidate nucleic acid mixture. In previously filed applications, U.S. Ser. No. 07/536,428, filed Jun. 11, 1990 and U.S. Ser. No. 07/714,131 filed Jul. 10, 1991, both of which are incorporated herein by reference, the inventors herein have taught a method for selective evolution of nucleic acids based upon binding properties of the nucleic acids themselves. The insight that cyclical selection and amplification can be a powerful tool for developing novel compounds when coupled with a partitioning system is herein adapted to evolving specific coding nucleic acids, based on the partitioning properties of polypeptide ligands binding to target molecules.

More specifically, the invention includes a method for making a polypeptide ligand of a desired target molecule which includes the following steps: First, synthesizing a mixture of translatable mRNA's, having certain sequence segments in common such as a ribosome binding site and a translation initiation codon and having a segment encoding a polypeptide at least part of which coding region is a randomized sequence. Second, employing the mRNA mixture in an in vitro translation system. Synthesis of nascent polypeptides ensues, each encoded by its own mRNA. At any time during translation, stable ribosome complexes can be isolated. It is preferred to isolate complexes in which translation has been stopped, or "stalled" by any of several known circumstances. Each isolated ribosome complex includes at least one ribosome, one nascent peptide and the coding mRNA which is now said to be translated mRNA. Although its chemical structure is unaltered, translated mRNA is bound to the ribosome complex in a different manner than it was bound prior to translation, as is known in the art. Third, the ribosome complexes are partitioned with respect to the binding of each nascent polypeptide to a desired target molecule. Some polypeptides bind weakly, some tightly, some not at all, with the target. The partitioning, however conducted, generally separates the mixture of ribosome complexes into ribosome complex-target pairs and unbound complexes. The set of ribosome complex-target pairs is thereby enriched for those polypeptides (and, necessarily their coding mRNA's) that can bind to the target. Fourth, the encoding mRNA's are separated from the complexes and amplified by conventional means for amplifying nucleic acids, such as reverse transcription and polymerase chain reaction (PCR). This amplification sets the stage for a subsequent round of transcription, polypeptide synthesis and partitioning to further enrich for target-binding polypeptide ligands. These cycles can be reiterated as many times as desired, until a desired binding affinity is achieved, or no further improvement in binding affinity is observed. The coding mRNA for any polypeptide selected in the foregoing manner can be cloned and sequenced, if desired. An individual polypeptide ligand can then be prepared in vivo from cloned coding mRNA, or by chemical or enzymatic methods in vitro.

In an alternate embodiment of the present invention, means for linking the nascent polypeptide to the translated mRNA are included in the design of the system. According to this method, a direct connection—either via covalent bonding or very tight affinity interactions—between the polypeptide and the mRNA allows for the removal of the ribosomal linkage between these two elements leaving mRNA·polypeptide copolymers. By removing the relatively large ribosome from the mRNA polypeptide copolymer, the ability to partition polypeptides based on the affinity of the randomized polypeptides to a given target may be greatly increased. In addition, the ribosome is then freed to translate additional mRNA species. The fewer ribosomes that can be utilized, the more randomized polypeptides can be generated in the process. In a specific example of this embodiment, a biotin molecule is covalently bound to the 5' end of the mRNA sequence utilized, and the nucleic acid template includes a fixed sequence in the translated region that encodes a polypeptide that may be covalently bound to biotin.

The present invention provides a class of products which are polypeptides, each having a unique sequence, each of which has the property of binding specifically to a desired target compound or molecule. Each compound of the invention is a specific ligand of a given target molecule. The invention is based on the unique insight that cyclical selection and amplification of nucleic acids can be applied to coding sequences by partitioning such coding sequences according to the binding affinities of the encoded polypeptides. In vitro evolutionary selection can therefore be applied for the first time to up to about $10^{18}$ different polypeptides. Polypeptides have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets. Most commonly, and preferably, for therapeutic applications, binding takes place in aqueous solution at conditions of salt, temperature and pH near acceptable physiological limits. For other uses different binding conditions can be employed.

The invention also provides a method which is generally applicable to make a polypeptide ligand for any desired target. The method involves selection from a mixture of candidates and step-wise iterations of structural improvement, using the same general selection theme, to achieve virtually any desired criterion of binding affinity and selectivity.

While not bound by a theory of operation, SPERT is based on the inventors' insight that within a polypeptide mixture containing a large number of possible sequences and structures there is a wide range of binding affinities for a given target. A polypeptide mixture comprising, for example a 10 amino acid randomized segment can have $20^{10}$ candidate possibilities. Those which have the higher affinity constants for the target are most likely to bind. After partitioning ribosome complexes or mRNA·polypeptide copolymers, dissociation of mRNA and reverse transcription/amplification/transcription, a second polypeptide mixture is generated by translation, enriched for the higher binding affinity candidates. Additional rounds of SPERT progressively favor the best ligands until the resulting polypeptide mixture is predominantly composed of only one or a few sequences. These can then be individually synthesized and tested for binding affinity as pure ligands. One cycle of SPERT effectively achieves reverse translation, at least quantitatively.

The ability to rapidly select a single sequence or family of sequences from a huge number of candidates has been dramatically shown in the nucleic acid area. In U.S. patent application Ser. No. 07/714,131 (referred to herein, along with U.S. patent application Ser. No. 07/536,428, as the SELEX Applications), nucleic acid ligands to a variety of targets—including both protein targets that are known to bind nucleic acids and protein targets that are not known to bind nucleic acids—have been identified. In such application there is also a description of a mathematical analysis of the partitioning and cycling aspects of SELEX referred to as SELEXION. This mathematical analysis dramatically demonstrated that by cycling through the partitioning process a number of times at a moderate stringency it is possible to obtain the individual species in a randomized mixture which have the highest affinity to the selected target.

In actual practice, the SELEX Applications show that although in some cases a single solution nucleic acid ligand may be identified, it is more often the case that a family of ligands is identified having similar affinity to the target. The family of ligands was shown to generally have the same three dimensional configuration and many conserved sequences. Surprisingly, in some cases where the target was a nucleic acid binding protein, the SELEX process was able to identify a ligand solution that had a higher affinity to the protein than the sequence that the protein binds to in nature. These results emphasize the practicality of "short cutting" the evolutionary process by screening a mixture containing a very large number of candidates.

Cycles of selection and amplification are repeated until a desired goal is achieved. In the most general case, selection/amplification is continued until no significant improvement in binding strength is achieved on repetition of the cycle. The iterative selection/amplification method is sensitive enough to allow isolation of two sequence variants in a mixture containing at least 65,000 sequence variants. The method could, in practice, be used to sample about $10^{18}$ different polypeptide species. There is no upper limit, in principle, to the number of different polypeptides which could be sampled, only a practical limit dictated by the sizes of reaction vessels and other containers necessary to perform the method. The polypeptides of the test mixture include a randomized sequence portion as well as conserved sequences as desired for combining with other functional domains or to provide sufficient polypeptide length to insure that the randomized sequence is accessible to the target in the ribosome complex or mRNA·polypeptide copolymer. Amino acid sequence variants can be produced in a number of ways including chemical or enzymic synthesis of randomized nucleic acid coding sequences. The variable sequence portion may contain fully or partially random sequence; it may also contain subportions of conserved sequence incorporated with randomized sequence. Sequence variation in coding nucleic acids can be introduced or increased by mutagenesis before or during the selection/amplification iterations.

In the case of a polymeric target, such as a protein, the ligand affinity can be increased by applying SPERT to a mixture of candidates comprising a first selected polypeptide sequence combined with a second randomized sequence. The sequence of the first selected ligand associated with binding or subportions thereof can be introduced into the randomized portion of the amino acid sequence of a second test mixture. The SPERT procedure is repeated with this second test mixture to isolate a second polypeptide ligand, having two sequences (one being the first polypeptide ligand) selected for binding to the target, which has increased binding strength or increased specificity of binding compared to the first polypeptide ligand isolated. The sequence of the second polypeptide ligand associated with binding to the target can then be introduced near the variable portion of the amino acid sequence after which cycles of SPERT results in a third polypeptide ligand. The third polypeptide ligand also contains the first and second ligand previously selected. These procedures can be repeated until a polypeptide ligand of a desired binding strength or a desired specificity of binding to the target molecule is achieved. The process of iterative selection and combination of polypeptide sequence elements that bind to a selected target molecule is herein designated "walking," a term which implies the optimized binding to other accessible areas of a macromolecular target surface or cleft, starting from a first binding domain. Increasing the area of binding contact between ligand and target can increase the affinity constant of the binding reaction. These walking procedures are particularly useful for isolating novel polypeptides which are highly specific for binding to a particular target molecule.

A variant of the walking procedure employs a ligand termed "anchor" which is known to bind to the target molecule at a first binding domain (See FIG. 8). This anchor molecule can in principle be any molecule that binds to the target molecule and which can be covalently linked directly or indirectly to a small bridge molecule for which a peptide binding sequence is known. When the target molecule is an enzyme, for example, the anchor molecule can be an inhibitor or substrate of that enzyme. The anchor can also be an antibody or antibody fragment specific for the target. The anchor molecule is covalently linked to the bridge molecule, chosen to bind an oligopeptide of known sequence. A test mixture of candidate polypeptides is then prepared which includes a randomized portion and includes also the known sequence that binds the bridging molecule. The bridging molecule binds the polypeptides to the target molecule in the vicinity of the anchor binding site. SPERT is then applied to select polypeptides which bind a surface of the target molecule adjacent to the anchor binding site. Polypeptide ligands which bind to the target are isolated. Walking procedures as described above can then be applied to obtain polypeptide ligands with increased binding strength or increased specificity of binding to the target. Walking procedures could employ selections for binding to the anchor binding site itself or to another part of the target itself. This method is particularly useful to isolate polypeptide ligands which bind at a particular site within the target molecule. The anchor acts to ensure the isolation of polypeptide sequences which bind to the target molecule at or near the binding site of the anchor.

Screens, selections or assays to assess the effect of binding of a polypeptide ligand on the function of the target molecule can be readily combined with the SPERT methods. Specifically, screens for inhibition or activation of enzyme activity can be combined with the SPERT methods.

In more specific embodiments, the SPERT method provides a rapid means for isolating and identifying polypeptide ligands which bind to nucleic acids and proteins, including enzymes, receptors, antibodies, and glycoproteins.

In another aspect, the present invention provides a method for detecting the presence or absence of, and/or measuring the amount of a target molecule in a sample, which method employs a polypeptide ligand which can be isolated by the methods described herein. Detection of the target molecule is mediated by its binding to a polypeptide ligand specific for that target molecule. The polypeptide ligand can be labeled, for example radiolabeled or enzyme linked, to allow qualitative or quantitative detection, analogous to ELISA and RIA methods. The detection method is particularly useful for target molecules which are proteins. The method is more particularly useful for detecting proteins which are known to be only weakly antigenic, or for which conventional monoclonal antibodies of a desired affinity are difficult to produce. Thus, polypeptide ligands of the present invention can be employed in diagnostics in a manner similar to conventional antibody-based diagnostics. One advantage of polypeptide ligands over conventional antibodies in such detection methods and diagnostics is that polypeptides are capable of being readily synthesized in vitro or after cloning, since the method of the invention concomitantly selects the means for amplification, e.g., coding nucleic acids, along with the ligand itself. Alternatively, the polypeptide can be chemically synthesized since its amino acid sequence can be ascertained readily from the nucleotide sequence of its coding mRNA. A SPERT-generated polypeptide ligand need not be as large as an antibody molecule. Another advantage is that the entire SPERT process is carried out in vitro and does not require immunizing test animals. Furthermore, the binding affinity of polypeptide ligands can be tailored to the user's needs. Compared to antibodies, SPERT-generated ligands have much greater versatility. Conventional antibodies are immunoglobulins, which, although capable of a large repertoire of binding affinities, are nevertheless variations of a narrow amino acid sequence and structural theme. SPERT-generated polypeptide ligands, in contrast, are unlimited as to structural type, and therefore have virtually unlimited potential for binding.

Polypeptide ligands of small molecule targets are useful as diagnostic assay reagents and have therapeutic uses as sequestering agents, drug delivery vehicles and modifiers of hormone action. Catalytic polypeptides are selectable products of this invention. For example, by selecting for binding to transition state analogs of an enzyme catalyzed reaction, catalytic polypeptides can be selected. Catalytic immunoglobulins have been developed by raising antibodies to transition state analogs (Schultz, P. C. (1989) Angew. Chem. Int. 2d Engl. 28:1283–1295; Schultz, P. G. (1989) Acc. Chem. Res. 22:287–294; Pollack, S. J. et al. (1989) Meth. Enzymol. 178:551–568).

In yet another aspect, the present invention provides a method for modifying the function of a target molecule using polypeptide ligands which can be isolated by SPERT. Polypeptide ligands which bind to a target molecule are screened to select those which specifically modify function of the target molecule, for example to select inhibitors or activators of the function of the target molecule. An amount of the selected polypeptide ligand which is effective for modifying the function of the target is combined with the target molecule to achieve the desired functional modification. This method is particularly applicable to target molecules which are proteins. A particularly useful application of this method is to inhibit protein function, for example to inhibit receptor binding or to inhibit enzyme catalysis. In this case, an amount of the selected polypeptide molecule which is effective for target protein inhibition is combined with the target protein to achieve the desired inhibition.

The term "reverse translation" is used throughout as shorthand for the concept of information flow from polypeptide sequence to nucleic acid sequence. The phrase and shorthand make reference to the original and revised "central dogma" pronounced by Francis Crick many years ago. Crick understood and articulated the idea that either RNA or DNA could serve as a template for the synthesis of complementary nucleic acid sequences, and that chemically either RNA or DNA could serve as a template for the synthesis of both RNA and DNA. Crick noted that proteins, comprised of strings of amino acids, were templated by nucleic acid but could not serve themselves as a template for the synthesis of nucleic acids.

Most importantly, no simple chemistry is known that allows "reverse translation"; that was the basis nearly 25 years ago of Crick's adaptor hypothesis for using information in RNA to yield specified protein sequences during translation.

SPERT has at its center a form of reverse translation that does not conflict with Crick's postulates. While no process, no simple chemistry, is known that provides synthesis of a nucleic acid containing a sequence specified by a polypeptide (whose sequence is unknown to the scientist at the time of reverse translation), SPERT provides a reliable mechanism for amplifying and using mRNAs that encode polypeptides of desired function but of unknown sequence. Techniques for binding one or a few polypeptides to a selected target are known in the art, although binding of a small number of polypeptides from a randomized pool of polypeptides is of no value by itself. It is the concomitant selection in the ribosome complex or mRNA-polypeptide copolymer of the mRNAs that encode those very polypeptides that provides a form of reverse translation because:

1) the selected coding sequences can be amplified to yield large quantities of both DNA and RNA;
2) the newly made mRNA can be used for synthesizing polypeptides, now a smaller set than the original randomized mixture of polypeptides from which non-binding, or poorly-binding polypeptides have been removed, and;
3) the polypeptides held in ribosome complexes or mRNA-polypeptide copolymers can be used for a subsequent round of SPERT.

Finally, "reverse translation" during SPERT does not yield a nucleic acid from only polypeptide sequence, but "reverse translation" does provide (through amplification techniques) net synthesis of the templates from which the desired polypeptide was synthesized. In principle a single molecule of polypeptide of the desired activity, along with a single template RNA in the translation complex or copolymer, will lead to a nanomole or even a micromole of nucleic acid corresponding to that polypeptide sequence. This net synthesis of nucleic acids based on the partitioning and activity of the desired polypeptide is an effective quantitative reverse translation that provides the materials for subsequent rounds of SPERT.

Also, the coding sequence can be used to deduce the amino acid sequence of a selected polypeptide. The polypeptide can then be synthesized by chemical methods, if desired.

These "P" complexes are immunoprecipitated by second antisera directed against the primary antisera, as shown in the bottom panel.

Figure 5:
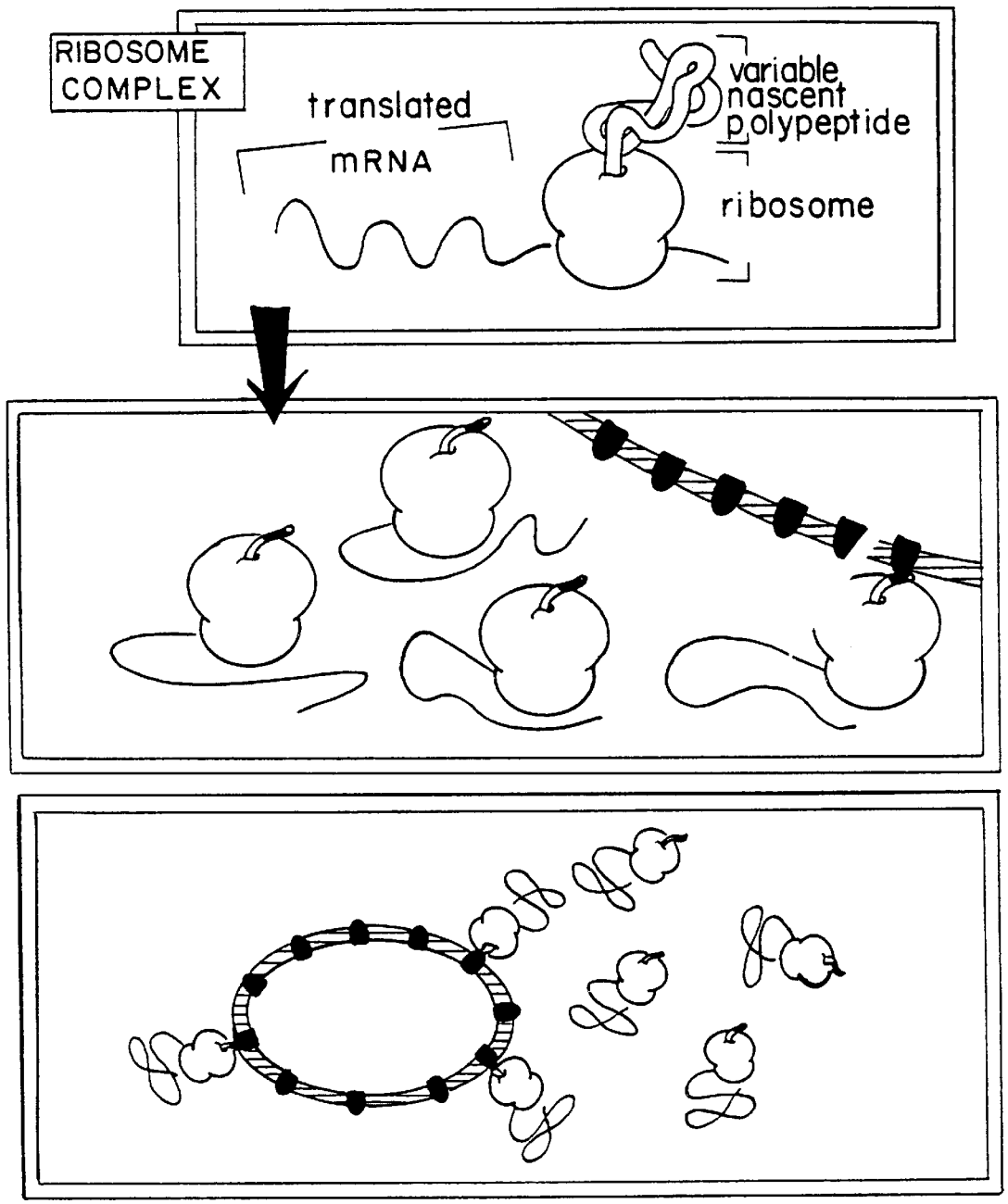

FIG. 5 is a diagram showing selection of polypeptide ligands by membrane partitioning. The top panel shows a ribosome complex as in FIG. 1. The middle panel shows ribosome complexes and membrane vesicles with membrane proteins. The membrane vesicles are depicted as a hatched band interrupted by hatched ovals that depict membrane proteins embedded in the membrane. In the middle panel, ribosome complexes are shown binding with membrane protein so that the nascent polypeptides having binding affinity for a membrane protein are partitioned. The bottom panel depicts three ribosome complexes bound to a membrane vesicle, forming a large complex which is separable from unbound ribosome complexes.

Figure 6:
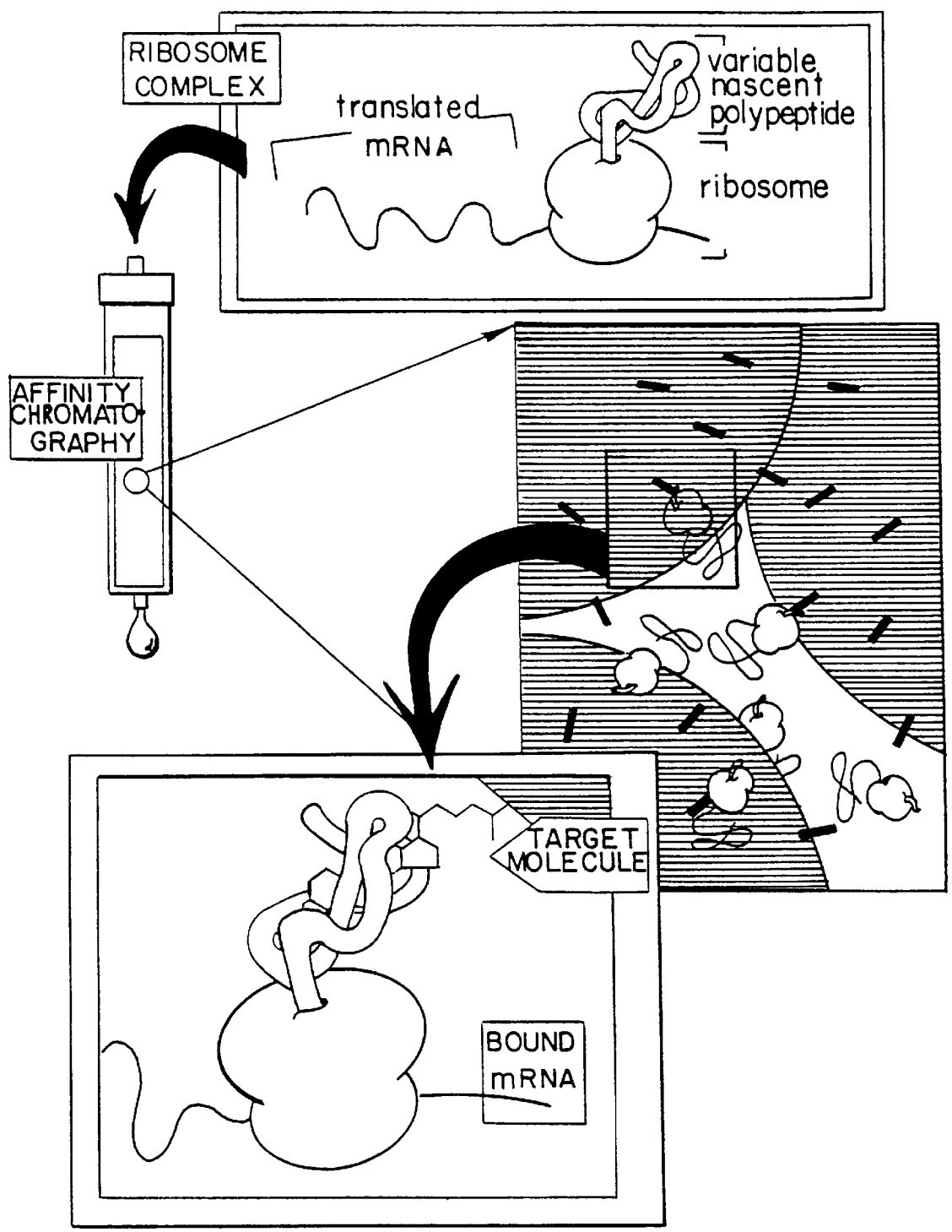

FIG. 6 is a diagram showing partitioning of polypeptide ligands by affinity column chromatography. Ribosome complexes (top panel) are passed through a column containing insoluble support materials to which have been bonded target molecules. The middle panel is an expanded view of the column showing support materials (hatched circular segments) with attached target molecules (black bars) to which some ribosome complexes are bound. The bottom panel shows, enlarged, a single ribosome complex in which the nascent polypeptide (light shading) is bound to a target molecule which is attached to a column support bead (hatched). Ribosome complexes with high affinity to the target molecules are retained on the column and subsequently eluted to continue with SPERT.

Figure 7:
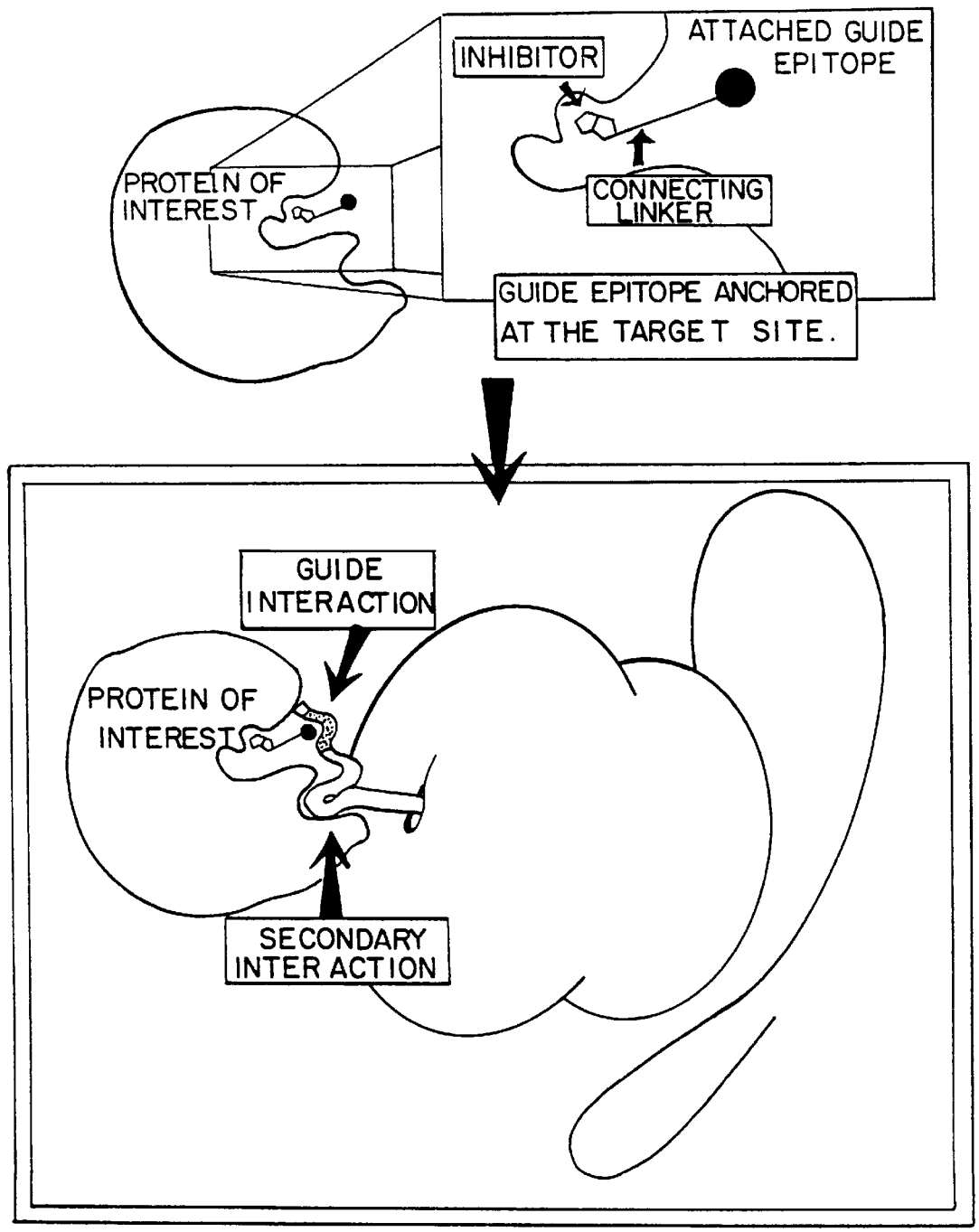

FIG. 7 is a diagram showing anchoring of a binding epitope and secondary ligand evolution. A molecule ("inhibitor") of known affinity for a target site on a protein is covalently linked to a "guide epitope". The guide epitope is any molecule for which there exists a peptide ligand, including a portion of a monoclonal antibody which contains an epitope recognition domain (Fab fragment). The mRNA encodes a reactive peptide sequence that binds the guide epitope, incorporated into the nascent polypeptide. The bottom panel depicts a ribosome complex having a nascent polypeptide that includes the reactive, guide binding, segment (shaded) and a randomized segment (unshaded). The ribosome complex is shown bound to the protein of interest by a binding interaction between the guide epitope and the reactive segment and by a secondary binding interaction between the randomized segment and a neighboring site on the target protein of interest. The randomized portion of the nascent polypeptide is free to evolve interactions with secondary sites on the target protein.

Figure 8:
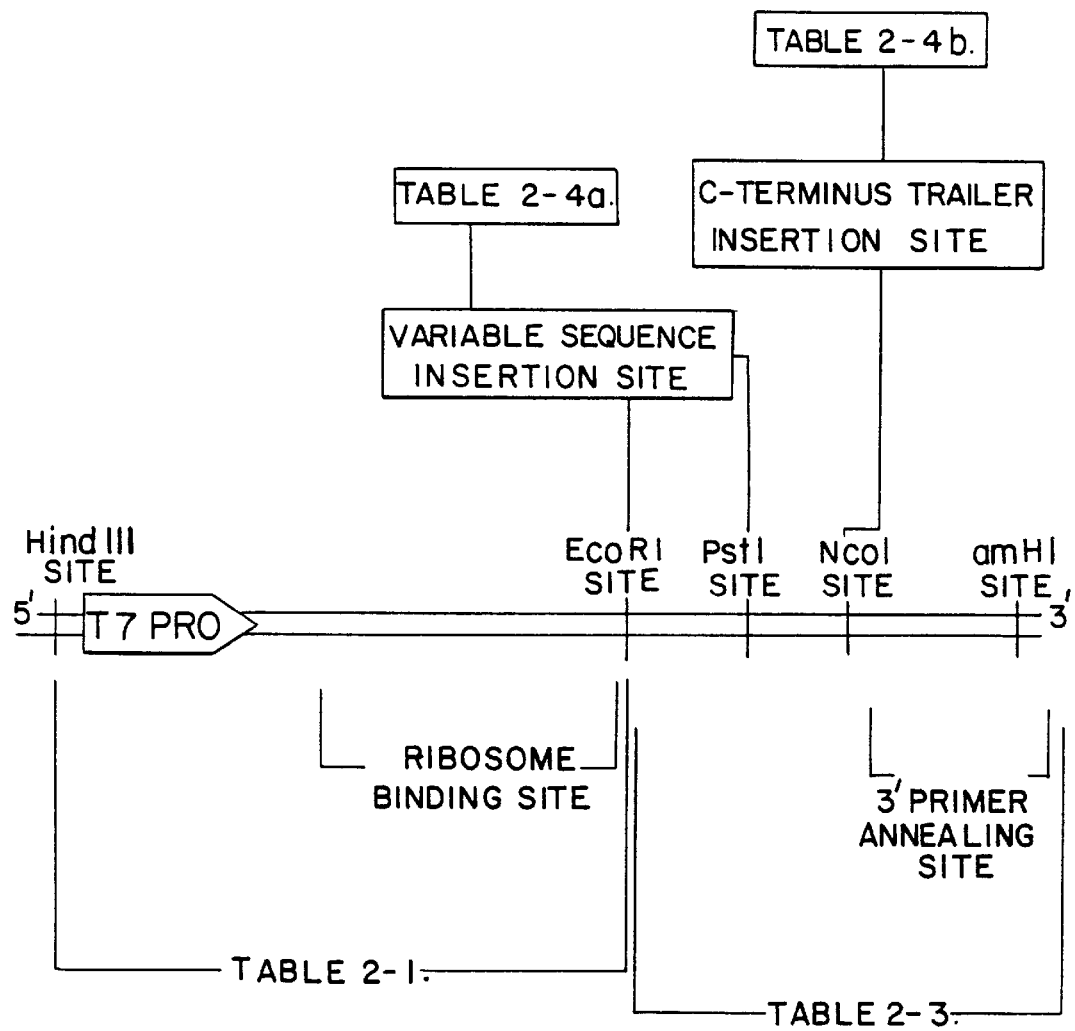

FIG. 8 is a diagram which shows the DNA to be transcribed and the relationships of the oligonucleotides of Tables 1 and 2 in the DNA, prior to inserting the randomized sequence. The depicted structure constitutes a cassette for carrying out the transcription, translation, reverse transcription and PCR processes used in SPERT.

DETAILED DESCRIPTION OF THE INVENTION

The following terms are used herein according to the definitions.

Polypeptide is used herein to denote any string of amino acid monomers capable of being synthesized by an in vitro translation system. The term also embraces post-translational modifications introduced by chemical or enzyme-catalyzed reactions, as are known in the art. Such post-translational modifications can be introduced prior to partitioning, if desired. Unless specified herein, all amino acids will be in the L-stereoisomeric form. Amino acid analogs can be employed instead of the 20 naturally-occurring amino acids. Any amino acid analog that is recognized by an aminoacyl-tRNA synthetase can be employed. Several such analogs are known, including fluorophenylalanine, norleucine, azetidine-2-carboxylic acid, S-aminoethyl cysteine, 4-methyl tryptophan and the like.

Ligand means a polypeptide that binds another molecule (target). In a population of candidate polypeptides, a ligand is one which binds with greater affinity than that of the bulk population. In a candidate mixture there can exist more than one ligand for a given target. The ligands can differ from one another in their binding affinities for the target molecule.

Candidate mixture is a mixture of nucleic acids and of polypeptides of differing sequence, from which to select a desired coding sequence and/or a desired ligand. The candidate mixture of nucleic acids serving as source of a candidate mixture of polypeptides can be in vitro transcription products of naturally-occurring nucleic acids or fragments thereof, chemically synthesized nucleic acids, enzymatically synthesized nucleic acids or nucleic acids made by a combination of the foregoing techniques. Target molecule means any compound of interest for which a ligand is desired. A target molecule can be a protein, fusion protein, peptide, enzyme, nucleic acid, nucleic acid binding protein, carbohydrate, polysaccharide, glycoprotein, hormone, receptor, receptor ligand, cell membrane component, antigen, antibody, virus, virus component, substrate, metabolite, transition state analog, cofactor, inhibitor, drug, controlled substance, dye, nutrient, growth factor, toxin, lipid, glycolipid, etc., without limitation.

Partitioning means any process whereby ribosome complexes or mRNA·polypeptide copolymers bound to target molecules, termed complex-target pairs herein, can be separated from ribosome complexes or mRNA·polypeptide copolymers not bound to target molecules. Partitioning can be accomplished by various methods known in the art. The only requirement is a means to separate complex-target pairs from unbound ribosome complexes or mRNA·polypeptide copolymers. Columns which selectively bind complex-target pairs but not ribosome complexes or mRNA·polypeptide copolymers, (or specifically retain ligand to an immobilized target) can be used for partitioning. A membrane or membrane fragment having the target on its surface can bind ligand-bearing ribosome complexes or mRNA·polypeptide copolymers forming the basis of a partitioning based on particle size. The choice of partitioning method will depend on properties of the target and of the complex-target pairs and can be made according to principles and properties known to those of ordinary skill in the art.

Amplifying means any process or combination of process steps that increases the amount or number of copies of a molecule or class of molecules. Amplifying coding mRNA molecules in the disclosed examples is carried out by a sequence of three reactions: making cDNA copies of selected mRNAs, using polymerase chain reaction to increase the copy number of each cDNA, and transcribing the cDNA copies to obtain an abundance of mRNA molecules having the same sequences as the selected mRNAs. Any reaction or combination of reactions known in the art can be used as appropriate, including direct DNA replication, direct mRNA amplification and the like, as will be recognized by those skilled in the art. The amplification method should result in the proportions of the amplified mixture being essentially representative of the proportions of different sequences in the mixture prior to amplification.

Specific binding is a term which is defined on a case-by-case basis. In the context of a given interaction between a given ligand and a given target, a binding interaction of ligand and target of higher affinity than that measured between the target and the candidate ligand mixture is observed. In order to compare binding affinities, the conditions of both binding reactions must be the same, and should be comparable to the conditions of the intended use. For the most accurate comparisons, measurements will be made that reflect the interaction between ligand as a whole and target as a whole. The polypeptide ligands of the invention can be selected to be as specific as required, either by establishing selection conditions that demand the requisite specificity during SPERT, or by tailoring and modifying the ligands through "walking" and other modifications using iterations of SPERT.

Randomized is a term used to describe a segment of a nucleic acid or polypeptide having, in principle any possible sequence over a given length. Randomized nucleic acid sequences will be of various lengths, as desired, ranging from about twelve to more than 300 nucleotides. The chemical or enzymatic reactions by which random sequence segments are made may not yield mathematically random sequences due to unknown biases or nucleotide preferences that may exist. Redundancy of the genetic code, and biases in the tRNA content of an in vitro translation system can introduce additional bias in the translated amino acid sequences. Introducing a deliberate bias into a randomized coding region can reduce the bias of the resulting translated amino acid sequence. The term "randomized" is used instead of "random" to reflect the possibility of such deviations from non-ideality. In the techniques presently known, for example sequential chemical synthesis, large deviations are not known to occur.

A bias may be deliberately introduced into a randomized sequence, for example, by altering the molar ratios of precursor nucleoside (or deoxynucleoside) triphosphates of the synthesis reaction. A deliberate bias may be desired, for example, to improve the randomness of amino acid sequence of translated polypeptides or to lower the frequency of appearance of certain amino acids.

For example, a randomized sequence biased for codons of the form ARN (where A is Adenine, R is Adenine or Guanine and N is any nucleotide) the most commonly encoded amino acids are basic (Arg, Asn, Lys) or polar (Ser). Randomized sequences biased for codons of the form GRN are biased for acidic amino acids, Asp (GAU, GAC) and Glu (GAA, GAG), and Glycine (GGN). Randomized sequences in which U is never the 1st base in the triplet codon will lack termination signals and will not encode amino acids Phe, Tyr, Cys and Trp. By such strategies, randomized coding sequences can be biased for the type of structure likely to bind a given target. For example, polypeptide sequences biased for acidic amino acids can bind cationic target molecules more easily than completely random polypeptides.

Translatable mRNA is RNA which possesses all requisite sequences for translation in a conventional in vitro translation system. These include, proper orientation and sequence proximal to the 5' end of the RNA, a ribosome binding site and an initiation codon. In prokaryotes, as is known in the art, other codons, such as UUG and GUG can serve as initiation codons and encode methionine if properly spaced within a ribosome binding site.

Ribosome binding site means a nucleotide sequence in the mRNA which functions as a binding site for a ribosome in an in vitro translation system. The sequences which function as ribosome binding sites differ depending on whether the ribosomes are of procaryotic or eucaryotic origin, as is known in the art. In procaryotic systems, the ribosome binding site is a short purine-rich region with a sequence such as GAGG or AGGA, usually located about 5–12 bases 5' to the initiation codon. The translation initiation codon is therefore usually located within 5–12 bases from the ribosome binding site in the 3' direction on the mRNA. These sequences are sometimes termed a Shine-Dalgarno sequence. The structures of ribosome binding sites and their proper placement to ensure correct initiation of protein synthesis are well known in the art.

Initiation codon is a characteristic trinucleotide sequence AUG which encodes methionine and which encodes a first amino acid of an encoded polypeptide and also sets the codon reading frame for the nucleotide sequence in the 3' direction from the initiation codon.

Ribosome complex is a macromolecular complex including at least one ribosome, attached mRNA molecule and, for each ribosome, a nascent polypeptide attached via tRNA to the ribosome. The nascent polypeptide has an amino acid sequence encoded by the attached mRNA. Ribosome complexes are formed, as is known in the art, during protein synthesis. Ribosome complexes are stable if they become stalled for any reason, for example, by depletion of release factor, lack of termination codon in the message, lack of a charged tRNA, etc., as known in the art. The mRNA together with attached ribosome(s) and nascent peptide(s) remain stably bound and can be isolated together, using methods known in the art.

mRNA·polypeptide copolymer is a macromolecular complex including an mRNA and a polypeptide having an amino acid sequence encoded by the attached mRNA. According to one embodiment of the invention, mRNA·polypeptide copolymers are formed by the creation of a candidate mixture in which the RNA includes fixed sequences and/or chemical modifications in both non-translated and translated regions so that a portion of the translated polypeptide will link with a portion of the mRNA via a covalent bond or tight affinity interaction. In other embodiments, the translated polypeptides or tRNA species utilized may be modified as well to facilitate the formation of mRNA·polypeptide or mRNA·tRNA·polypeptide copolymers.

In vitro translation can be carried out using known systems. These well-known translation systems are the *E. coli* system, the wheat germ system, and the rabbit reticulocyte system. The latter is available commercially. The conditions for carrying out in vitro translations are well-known in the art, and various modifications, adaptations and optimizations are available to those skilled in the art.

The combination of translatable mRNA encoding a polypeptide and in vitro translation system constitute amplifying means for amplifying the quantity of polypeptide encoded by the mRNA. The mRNA can itself be amplified using reverse transcription, PCR with appropriate primers and an RNA polymerase. The amplified mRNA can serve for in vitro synthesis of desired quantities of the encoded polypeptide. As noted, supra, this process constitutes reverse translation.

The terms "ribosome" and "nascent peptide" have conventional meanings known in the art. The term "translated mRNA" simply refers to mRNA present in a ribosome complex, either wholly or partially translated.

Ribosome complex-target pairs are ribosome complexes of which the nascent polypeptide component is bound to a target molecule. The target molecule can be free in solution or bound to a solid support matrix.

Homology is used to compare the related uses of sequences. Percent amino acid sequence homology is measured by comparing sequences of equal length position by position. The percent of those positions occupied by the same amino acid in two polypeptides is the percent sequence homology. Thus, given peptide ABCDE as a naturally-occurring comparison peptide, peptides ABCDX or ABXDE are 80% homologous but peptides ABXYZ, AXYZE and XYZDE are 40% homologous and peptides EDCBA, BDAEC, MNOPQ are non-homologous.

The SPERT method involves the combination of a selection of polypeptide ligands which bind to a target molecule, for example a protein, with amplification of those selected polypeptides via the attached mRNAs. Iterative cycling of the selection/amplification steps allows selection of one or a small number of polypeptides which bind most strongly to the target from a pool which contains a very large number of nucleic acids and hence encoded polypeptides.

Cycling of the selection/amplification procedure is continued until a selected goal is achieved. For example, cycling can be continued until a desired level of binding of the polypeptides in the test mixture is achieved or until a minimum number of polypeptide components of the mixture is obtained (in the ultimate case until a single species remains in the test mixture). In many cases, it will be desired to continue cycling until no further improvement of binding is achieved. It may be the case that certain test mixtures of polypeptides show limited improvement in binding over background levels during cycling of the selection/amplification. In such cases, the sequence and length variation in the test mixture should be increased until improvements in binding are achieved. Anchoring protocols and/or walking techniques can be employed as well.

Specifically, the method requires the initial preparation of a test mixture of candidate polypeptides. A translatable mRNA mixture is prepared, each member of the mixture including in its nucleotide sequence a ribosome binding site, an initiation codon and a randomized coding region. Preferably the individual mRNA's contain a randomized region flanked by sequences conserved in all nucleic acids in the mixture. The conserved regions are provided to facilitate amplification of selected nucleic acids. Since there are many such sequences known in the art, the choice of sequence is one which those of ordinary skill in the art can make, having in mind the desired method of amplification. The randomized coding region can have a fully or partially randomized sequence according to the desired translation product. Depending on the desired polypeptide structure, the coding portion of the nucleic acid can contain subportions that are randomized, along with subportions which are held constant in all nucleic acid species in the mixture. For example, sequence regions known to code for amino acid sequences that bind, or have been selected for binding, to the target can be integrated with randomized coding regions to achieve improved binding or improved specificity of binding. Sequence variability in the polypeptide test mixture can also be introduced or augmented by generating mutations in the coding mRNA's during the selection/amplification process. In principle, the mRNA's employed in the test mixture can be any length as long as they can be amplified. The method of the present invention is most practically employed for selection from a large number of sequence variants. Thus, it is contemplated that the present method will preferably be employed to assess binding of polypeptide sequences ranging in length from about four amino acids to any attainable size.

The randomized portion of the coding nucleic acids in the test mixture can be derived in a number of ways. For example, full or partial sequence randomization can be readily achieved by direct chemical synthesis of the nucleic acid (or portions thereof) or by synthesis of a template from which the nucleic acid (or portions thereof) can be prepared by use of appropriate enzymes. Chemical synthesis provides the advantages of being precisely controllable as to length and allowing individual randomization at each triplet position. A commercial DNA synthesizer can be used, either with an equivalent mixture of the four activated nucleotide substrates or with a biased mixture. Alternatively, the synthesizer can be set up to provide a limited nucleotide selection at a given position, e.g., only A at the first triplet position. End addition, catalyzed by terminal transferase in the presence of nonlimiting concentrations of all four nucleotide triphosphates can add a randomized sequence to a segment. Sequence variability in the coding nucleic acids can also be achieved by employing size-selected fragments of partially digested (or otherwise cleaved) preparations of large, natural nucleic acids, such as genomic DNA preparations or cellular RNA preparations. In those cases in which randomized sequence is employed, it is not necessary (or possible from long randomized segments) that the test mixture contains all possible variant sequences. It will generally be preferred that the test mixture contain as large a number of possible sequence variants as is practical for selection, to insure that a maximum number of potential amino acid sequences of the translated polypeptide are identified. A randomized sequence of 60 nucleotides will contain a calculated $10^{36}$ different candidate nucleic acid sequences which would encode $10^{26}$ possible decapeptides. As a practical matter, it is possible to sample only about $10^{18}$ polypeptide candidates in a single selection. Therefore, candidate mRNA mixtures that have randomized segments longer than 60 contain too many possible sequences for all to be sampled in one selection. Many epitopes recognized by antibodies are only 5–10 amino acids in length. It is not necessary to sample all possible sequences of a candidate mixture to select a polypeptide ligand of the invention. It is basic to the method that the coding nucleic acids of the test mixture are capable of being amplified. Thus, it is preferred that any conserved regions employed in the test nucleic acids do not contain sequences which interfere with amplification.

The practical considerations that limit the number of candidates that may be sampled include the volume or mass of materials that can be handled in a laboratory environment. A system that operates to form ribosome complexes requires a stoichiometric amount of ribosome in the translation mixture. The presence of this quantity of ribosomes severely limits the amount of sequences that can be sampled—to about $10^{12}$ to $10^{14}$ complexes. The production and isolation of quantities of ribosomes in excess of these amounts would be impractical. As $E.$ $coli$ has only about $10^4$ ribosomes per cell, a huge amount of $E.$ $coli$ would be required to produce stoichiometric amounts of ribosomes. The limitation of $10^{12}$ to $10^{14}$ complexes is higher than the limitations found in other systems that have been devised for sampling large numbers of randomized polypeptides. However, when the ribosome is not bound up in the ribosome complex but is free to translate a large number of mRNA species in the reaction mixture, the number of mRNA species that can be practically tested at a time rises to at least about $10^{17}$ to $10^{18}$ different candidate sequences, depending on the number of mRNAs translated by a single ribosome.

The complex of a ribosome, mRNA, and nascent polypeptide attached to a tRNA in the P-site of the ribosome is very stable. Release of the nascent peptide from the complex and of the mRNA from the ribosome requires protein release factors. Release factor recognition requires the positioning of the stop codons of the mRNA in the A-site of the ribosome. In the absence of a stop codon or release factor the dissociation of the translation complex from mRNA is very slow. The addition of the antibiotics cycloheximide (eukaryotic systems) and chloramphenicol (prokaryotic system) further stabilizes the complexes so that extensive manipulations like column chromatography and gradient centrifugation can be performed.

In this embodiment a ribosome is preferably paused at the end of a coding sequence on a mRNA with the encoded nascent polypeptide available for partitioning of the complex. There are a number of ways in which this can be accomplished. Because stop codons are essential for release factor action, a translating ribosome that does not encounter any stop codons will proceed to the end of a mRNA and stall at the 3' end (Connolly and Gilmore, supra). In vitro translation systems which have been depleted of release factor (by immunoinactivation or mutation) will result in the stalling of translation complexes at stop codons. Removal of GTP, the use of non-hydrolyzable analogues, and the use of certain antibiotics will also stall translational complexes. The timed addition of these exogenous factors to a synchronous in vitro translation reaction can produce predictable sizes of nascent polypeptide for the successful partitioning of the translational complex. In some organisms there exist temperature-sensitive tRNA synthetase mutants. Another way of stalling translational complexes at defined sites is to include at the 3' end of the coding region a stretch of sense codons which are recognized by a single species of tRNA for which there exists a conditional tRNA synthetase mutant. In vitro translation reactions done from extracts of such mutants under the restrictive condition will result in stalled complexes at the stretch of sense codons for that particular tRNA.

It will be understood that it is not necessary to stall or pause the translation process to obtain partitionable ribosome complexes. Stable complexes can be isolated at any time during active translation. It is advantageous to isolate actively translating ribosome complexes when it is desired to vary the length of the randomized segment, e.g., to test the effects of polypeptide length on binding efficacy. Ribosome complexes isolated during active translation constitute a population of nascent peptides of varied length. By synchronously initiating translation and isolating ribosome complexes at various times thereafter, the effects of increasing polypeptide length can be compared.

Polymerase chain reaction (PCR) is an exemplary method for amplifying nucleic acids. Descriptions of PCR methods are found, for example in Saiki et al. (1985) Science 230:1350–1354; Saiki et al. (1986) Nature 324:163–166; Scharf et al. (1986) Science 233:1076–1078; Innis et al. (1988) Proc. Natl. Acad. Sci. 85:9436–9440; and in U.S. Pat. No. 4,683,195 (Mullis et al.) and U.S. Pat. No. 4,683,202 (Mullis et al.). In its basic form, PCR amplification involves repeated cycles of replication of a desired single-stranded DNA (or cDNA copy of an RNA) employing specific oligonucleotide primers complementary to the 3' ends of both strands, primer extension with a DNA polymerase, and DNA denaturation. Products generated by extension from one primer serve as templates for extension from the other primer. A related amplification method described in PCT published application WO 89/01050 (Burg et al.) requires the presence or introduction of a promoter sequence upstream of the sequence to be amplified, to give a double-stranded intermediate. Multiple RNA copies of the double-stranded promoter-containing intermediate are then produced using RNA polymerase. The resultant RNA copies are treated with reverse transcriptase to produce additional double-stranded promoter containing intermediates which can them be subject to another round of amplification with RNA polymerase. Alternative methods of amplification include among others cloning of selected DNAs or cDNA copies of selected RNAs into an appropriate vector and introduction of that vector into a host organism where the vector and the cloned DNAs are replicated and thus amplified (Guatelli, J. C. et al. (1990) Proc. Natl. Acad. Sci. 87:1874). In general, any means that will allow faithful, efficient amplification of selected nucleic acid sequences can be employed in the method of the present invention. It is only necessary that the proportionate representations of sequences after amplification reflect the relative proportions of sequences in the mixture before amplification.

Specific embodiments of the present invention for amplifying RNAs are based on Innis et al. (1988) supra. The RNA molecules in the test mixture are designed to contain a sequence transcribed from a T7 promoter in their 5' portions. Full-length cDNA copies of selected mRNA molecules are made using reverse transcriptase primed with an oligomer complementary to the 3' sequences of the selected RNAs. The resultant cDNAs are amplified by Taq DNA polymerase chain extension, employing a primer containing the T7 promoter sequence as well as a sequence complementary to the conserved 5' and of the selected RNAs. Double-stranded products of this amplification process are then transcribed in vitro. Transcripts are used in the next selection/amplification cycle. The method can optionally include appropriate nucleic acid purification steps.

In general, any protocol which will allow selection of polypeptides based on their ability to bind specifically to another molecule, i.e., a protein or any target molecule, can be employed in the method of the present invention. It is only necessary that the ribosome complexes or mRNA-polypeptide copolymers be partitioned without disruption such that the selected coding mRNA's are capable of being amplified. For example, in a column binding selection in which a test mixture of ribosome complexes bearing nascent randomized polypeptide is passed over a column of immobilized target molecules, the complexes bearing polypeptide ligands of the target are retained and the non-target binding complexes are eluted from the column with appropriate buffer. A wide variety of affinity chromatography techniques, including support matrices and coupling reactions is available for application of a column partitioning system. Target binding polypeptides together with mRNA's encoding each remain bound to the column. The relative concentrations of protein to test polypeptides in the incubated mixture influences the strength of binding that is selected for. When polypeptide is in excess, competition for available binding sites occurs and those polypeptides which bind most strongly are selected. Conversely, when an excess of target is employed, it is expected that any polypeptide that binds to the target will be selected. The relative concentrations of target to polypeptide employed to achieve the desired selection will depend on the type of target, the strength of the binding interaction and the level of any background binding that is present. The relative concentrations needed to achieve the desired partitioning result can be readily determined empirically without undue experimentation. Similarly, it may be necessary to optimize the column elution procedure to minimize background binding. Again such optimization of the elution procedures is within the skill of the ordinary artisan.

An unexpected feature of the invention is the fact that the polypeptide ligand need not be elutable from the target to be selectable. This is because it is the mRNA that is recovered for further amplification or cloning, not the polypeptide itself. It is known that some affinity columns can bind the most avid ligands so tightly as to be very difficult to elute. However the method of the invention can be successfully practiced to yield avid ligands, even covalent binding ligands. Ribosome complexes can be disrupted by denaturing agents such as urea or sodium dodecyl sulfate without affecting the integrity of the mRNA. Various mRNA-polypeptide copolymers may be separated into their component units based on the specific nature of linking between the RNA and the associated polypeptide. The mRNA's of selected ligands are amplified, as described elsewhere herein, to yield a mixture of coding sequences enriched for those that encode polypeptide ligands of the desired target, including ligands that bind tightly, irreversibly or covalently.

Immunoreactivity of nascent polypeptides on ribosome complexes or mRNA-polypeptide copolymers can be used to purify the encoding mRNAs. In one embodiment, ribosome complexes are purified from cells in the presence of inhibitors such as chloramphenicol or cycloheximide which stall translational complexes on mRNA. Binding of antibodies which recognize the epitope of interest followed by binding antibodies which recognize those antibodies results in immunoprecipitation of the ribosome complexes containing the mRNAs which encode the epitope. The background of mRNAs which do not encode the epitope of interest but are trapped by the immunoprecipitated complex can be lowered by using purified IgGs against the epitope followed by purification of the immunoreactive ribosomes on a protein A column. (IgGs are one class of the soluble immunoglobulins which compose antisera. Protein A is derived from *Staphylococcus aureus* and has a high affinity for IgGs. Protein A binding does not interfere with epitope recognition.)

Figure 4:
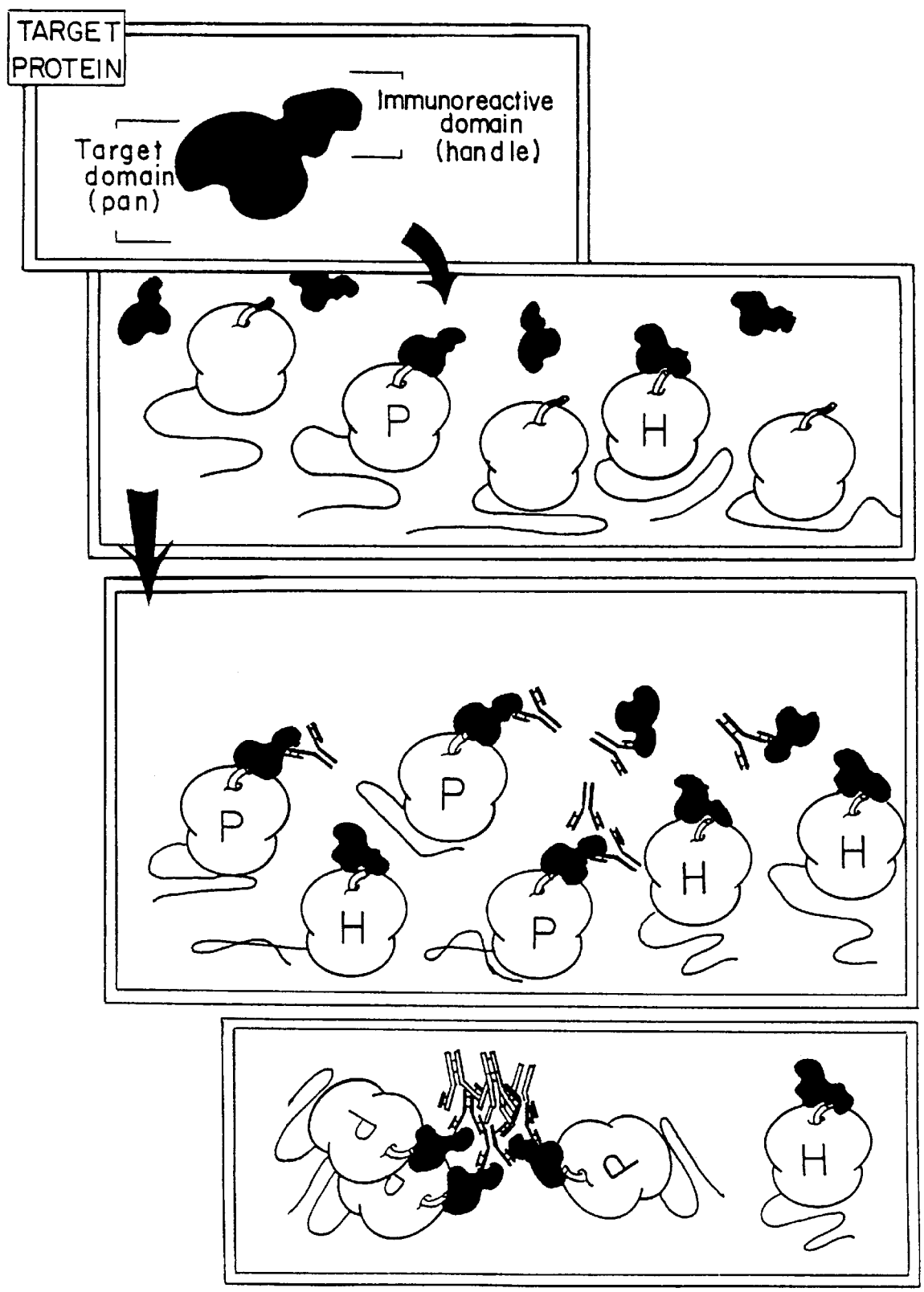
FIG. 4 is a diagram showing partitioning of polypeptide ligands by indirect immunoprecipitation. The top panel shows a target protein which has an immunoreactive domain ("handle") and a target domain ("pan"). Three types of ribosome complexes are depicted in the second panel. Those with no affinity for the target protein are shown in white. Those with affinity for the "pan" are shown in light gray labeled with a "P" and shown with a bound target protein attached by the "pan" to the nascent peptide. Those with affinity for the "handle" are dark gray, labeled with an "H" and shown with a bound target protein attached by the "handle" to the nascent peptide. In the third panel, a first antibody (black lines) directed against the "handle" either displaces ligand associations of the "H" complexes or those complexes are unreactive. The first antisera form a sandwich with the "P" complexes made up of a ribosome complex associated with the target protein, through its "pan", and bound to the first immunoglobulin through the "handle".

These procedures for immunoprecipitation to partition ribosome complexes or mRNA-polypeptide copolymers can be used in a variety of modifications to partition the translational complexes in SPERT. One such modification is termed "panhandling" (See FIG. 4). A protein is composed of an immunoreactive domain for which known antibody exists, and a separate target domain for which one wishes to evolve protein ligands. Ribosome complexes or mRNA-polypeptide copolymers which interact with the target domain (the "pan") via their nascent polypeptides will be immunoprecipitated upon binding antibodies which recognize the immunoreactive domain (the "handle"). This modification is especially useful for developing polypeptide ligands against a segment of a fusion protein in which the amino terminus is the fragment of a common protein (beta-galactosidase, for example) and the carboxyl-terminal portion is the protein of interest. It will also be useful for the development of polypeptide ligands which recognize immunoresistant domains of a protein which has an immunodominant domain for which polyclonal sera is available. Where immunoprecipitation is employed, it will be advantageous to discard any ribosome complexes or mRNA-polypeptide copolymers that react directly with the antibodies, prior to selection.

Alternative partitioning protocols for separating polypeptides bound to targets, particularly proteins, are available to the art. For example, binding and partitioning can be achieved by immunoprecipitation of the test ribosome complex mixture or test mRNA-polypeptide copolymers mixture and passing the immune complexes through a protein A affinity column which retains the immune reactive polypeptide-containing complexes as the column. Those mRNA's that encode a polypeptide that binds to the target antibody will be retained on the column as part of the ribosome complex or mRNA-polypeptide copolymer and unbound coding mRNA's can be washed from the column.

Interestingly, protein loops may be a powerful location for randomization and SPERT-based isolation of novel ligands. When inspecting protein structures in detail, only secondary structures are predictable; those structures include alpha helices and beta sheets or multiple strands, and either structure can be formed with parallel or anti-parallel peptides. The connectors between such secondary structures, called loops or hairpins, are related to RNA hairpin loops and RNA pseudoknots in that the locations of the ends of the loops are set by the secondary structures but the exact loop structures are idiosyncratic and dependent on the loop primary sequences and contacts with other elements of the protein. Loop sequences, when randomized and put through SPERT should provide vast structural libraries. Disulfide bonds between cysteines represent another means by which to construct loops; similarly, zinc fingers and copper or other metal "fists" also provide other kinds of loops.

Effective partitioning can be carried out with pure or impure target preparations. In cases where target preparations are impure, selectivity can be enhanced by strategies that enhance the binding of ligands to the desired target, or which specifically elute desired ligands or prevent their binding. The latter approach is subtractive. A known ligand can block binding of any polypeptide that can bind the target so that the desired polypeptide is partitioned by elution and unwanted polypeptides are retained on the column.

Optionally, chemical or enzymic modifications of the polypeptide can be introduced post-translationally. The process for making such modifications should not disrupt the ribosome complexes or mRNA-polypeptide copolymers. An important type of post-translational modification is oxidation to form disulfides in sequences that contain two or more cysteines. Particularly for small polypeptides, disulfide bonds are especially advantageous to lock in a desired conformational state so that a rigid structure having high specificity and binding affinity for a target can be achieved. (See, e.g., Olivera, B. M., et al. (1990) Science 249:257–263.

Other forms of post-translational structure modifications include introducing factors that non-covalently influence tertiary structure of the nascent polypeptide. In particular, metal ions such as $Ca^{++}$, $Mg^{++}$, $Mn^{++}$, $Zn^{++}$, $Fe^{3O+}$, $Fe^{+++}$, $Cu^{++}$ and $Mo^{6+}$ can affect polypeptide folding configuration by forming coordination complexes with amino acid side chains. Similarly organic compounds such as nicotinamide nucleotides, flavine nucleotides, porphyrins, thiamine phosphates, serotonin, and the like, including inhibitors, agonists and antagonists of known biological functions, can interact with the nascent polypeptide to modify its 3-dimensional folded configuration. As thus modified, the nascent polypeptide can exhibit different binding properties than an unmodified polypeptide. The use of such configurational modifiers enhances the range of potential binding activities of any candidate mixture of polypeptides. Also, it affords a means for selecting polypeptides having conditionally reversible functions, i.e., capable of being functionally "off" or "on", depending on the presence or absence of the modifier. Configurational modifiers need not be naturally-occurring compounds. The use of such modifiers during partitioning is only limited by the need to maintain stability of the ribosome complexes. Modifiers which disrupt ribosome complexes or which degrade the coding mRNA or nascent polypeptide should be avoided. A modifier can be included in the buffer or medium during partitioning. Alternatively, SPERT itself can be used to pre-select polypeptides which bind the modifier as a target after which the candidate mixture of selected modifier-binding polypeptides can be further selected, via SPERT, for binding the ultimate target.

Sequence variation in the test coding mRNA mixture can be achieved or increased by mutation. For example, a procedure has been described for efficiently mutagenizing nucleic acid sequences during PCR amplification (Leung et al. 1989). This method or functionally equivalent methods can optionally be combined with amplification procedures in the present invention.

Alternatively, conventional methods of DNA mutagenesis can be incorporated into the nucleic acid amplification procedure. Applicable mutagenesis procedures include, among others, chemically induced mutagenesis and oligonucleotide site-directed mutagenesis.

The starting mRNA mixture is not limited to sequences synthesized de novo. In particular, SPERT can be used to modify the function of existing proteins. A segment of the natural sequence is replaced by a corresponding segment of randomized sequence in the mRNA that encodes the protein. Since many known proteins belong to families having some sequences conserved and others varied, the logical approach is to replace the variable (or hypervariable) regions with randomized sequence, to maximize the chance of altering function. The proper choice of partitioning conditions, as will be apparent to those skilled in the art, results in selection for the desired functional variant. In this way, modifications, alterations and improvements on known proteins can be achieved.

To proceed to the amplification step when utilizing ribosome complexes, coding nucleic acids must be released from the target-bound ribosome complexes after partitioning. This process must be done without chemical degradation of the coding mRNA's and must result in amplifiable nucleic acids. In a specific embodiment, selected coding RNA molecules are eluted from a column using a high ionic strength buffer or other eluant capable of disrupting the ligand-target bond. Alternatively, the ribosome can be denatured such that the mRNA is eluted. The coding mRNA can be removed from ribosome complexes or from ribosome complex-target pairs by phenol extraction or by phenol combined with a protein denaturing agent such as 7M urea. Although ribosomal RNA is also extracted, subsequent amplification is selective for the mRNA's because the primers used for cDNA synthesis and PCR amplification are complementary only to a conserved sequence in the mRNA's and not to ribosomal RNA.

As the translation of randomized mRNAs proceeds during the SPERT protocol, the growing polypeptide makes its way from the peptidyl transferase site within the large ribosome subunit toward the cytoplasmic solvent. The peptidyl transferase site is an intrinsic activity of the large ribosome subunit from all organisms; that site has been defined functionally but its precise location within the ribosome is unknown. However, the distance between that site and the cytoplasmic solvent also is known to be about 30 to 40 amino acids in length.

For optimal effectiveness in SPERT, the random portion of the nascent polypeptide (whose properties are selected during the procedure) should be "outside" the ribosome in order for partitioning of the ribosome complex to fully utilize the properties of the randomized polypeptide. A C-terminal trailer sequence is preferably incorporated into the translated polypeptide to insure that the randomized sequence is fully exposed after translation. From the work of Smith et al, (PNAS, 75:5922, 1978) and Malkin and Rich (J. Mol. Biol., 26:329, 1967) for both prokaryotes and eukaryotes: about 30 to 40 amino acid residues remain within the ribosome during translation. Furthermore, if the amino-terminus of a growing polypeptide contains a hydrophobic domain of about 20 amino acid residues, a nascent polypeptide of about 50 residues has been shown to be enough to allow the translation complex to interact with a membrane by hydrophobic interactions, see Kurzchalia et al, Nature 320:634, 1986). Thus, in those preferred embodiments of SPERT utilizing ribosome complexes, the randomized polypeptide will be encoded by randomized mRNA that is about 30–40 codons (that is, about 90–120 nucleotides) upstream from the codons at which the translation complex stalls. It will be understood that both longer and shorter C-terminal trailer sequences can be used effectively, and that SPERT, itself, can be used to determine optimum trailer length for a given partitioning system. The sequence of mRNA and encoded polypeptide in the C-terminal trailer can be designed to have any other desired function, such as more stability in the translation complex, ease of in vitro manipulation, subsequent polypeptide purification, as a reporter activity for diagnostics, cell entry, etc.

Polypeptides selected by SPERT can be produced by any peptide synthetic method desired. Chemical synthesis can be accomplished since the amino acid sequence of the polypeptide is readily obtainable from the nucleotide sequence of the coding mRNA. Since cDNA from the coding mRNA is available, the polypeptide can also be made by expressing the cDNA in a suitable host cell.

SPERT offers, as noted above, an opportunity to sample as many as $10^{18}$ peptide sequences during a rigorous experiment with a particular target. As such SPERT may be compared with in vivo technologies aimed at uncovering peptides with specific binding properties. These technologies, lumped together under the name "phage display systems", have been available for more than five years (see, Smith, Science 228:1315, 1985) and widely appreciated in the last year (See, e.g., Charbit et al., EMBO J. 5:3029, 1986; Parmley et al., Gene 73:305, 1988; Scott et al., Science 249:386, 1990; Devlin et al., Science 249:404, 1990; Cwirla et al., Proc. Natl. Acad. Sci. 87:6378, 1990). Because phage display systems depend, in their present form, on a transformation step with either plasmid or phage DNA, the intrinsic depth of those systems is less than in SPERT. Phage display systems allow $10^9$ different peptides to be searched easily, and perhaps $10^{11}$ or so with bigger volumes and more difficulties. SPERT thus has a value for looking rigorously through large libraries.

Both SPERT, as defined thus far, and the phage display systems have a disadvantage in common, at least formally. In SPERT the peptide of interest is held by the ribosome, a machine that contains its own proteins and which is extremely large relative to the peptide of interest. Similarly, in the phage display systems the peptide of interest protrudes from a phage particle which is also relatively extremely large and which contains its own proteins. Although each of these systems will yield a peptide of interest with careful partitioning of the bound peptide from all other peptides bound to ribosomes or phage capsids, an improved system would provide the peptide of interest bound to an encoding nucleic acid (to achieve reverse translation) free of any other large, proteinaceous components. As described above, the large phage particle and the ribosome add limitations to these systems other than in the partitioning step of the process. The large entities also severely limit the number of random peptides that may be practically generated and tested in the screening process.

SPERT lends itself to such an improvement. In an alternate embodiment, this invention contemplates a simple and general mechanism by which a non-random portion of each peptide within the collection of peptides becomes covalently or very tightly attached to one end or the other of the mRNA that encodes it to form mRNA polypeptide copolymers.

There are an almost unlimited number of specific systems that could be employed to generate mRNA·polypeptide copolymers. Any such system that allows the ribosomes in the translation mixture to have a high turnover can be useful. The in vitro reactions should be as free as possible from RNases. The RNAse problem may also be alleviated by using mutant strains to lower RNase levels. Alternately, various techniques familiar to those skilled in the art are available for making the mRNA nuclease resistant. Additional criteria for effective systems for forming mRNA·polypeptide copolymers include the following: 1) the interactions between the nascent polypeptide and the mRNA must either occur before the ribosome complex is disrupted, or at a rate that highly favors the interaction over dissociation of the proximal species; 2) additional reagents should be relatively small; and 3) the reaction between the nascent polypeptide and the mRNA should be relatively efficient (i.e., at least about 5% or greater).

A nonlimiting catalog of methods that can be employed to generate mRNA·polypeptide copolymers will generally fall into the following categories: 1) Adapted post-translational modification systems; 2) Activation of the 5' end of the mRNA species and the N-terminus of the peptides to promote relatively simple organic chemical type reactions between the species; 3) Attachment of the peptide to the mRNA prior to the onset of translation; and 4) tRNA crosslinking of the nascent polypeptide and the mRNA. Various embodiments of each of these systems is described below. The design of additional embodiments of these general systems would also be obvious to those skilled in the art.

Post Translational Modification Systems

In one embodiment the collection of mRNAs used in SPERT is synthesized using T7 RNA polymerase and 5' guanosine phosphono monothioate for initiation (see, Burgin et al., EMBO J. 7:4111, 1990, for example), the monothioate is incorporated only at the 5' end; nucleoside triphosphates are the source of all internal residues during transcription. Organic tags may be attached to the 5' end without difficulty, and without harming the RNA for other functions. Thus each mRNA in the collection could have, for example, biotin or any one of a number of small reagents affixed to the 5' end of the RNA. Alternatively, mononucleotides labeled with biotin could be used to initiate transcription. The 5' end of the RNA would certainly not preclude translation by bacterial ribosomes, since those ribosomes are indifferent to the chemical nature of the 5' end as long as enough nucleotides are present upstream of the initiating AUG and as long as those nucleotides contain appropriate sequences to cause initiation to occur.

According to this embodiment, the codons downstream from the AUG, also fixed, encode a peptide that has an extremely high affinity for or can be covalently bound to the chemical adduct positioned at the 5' end of each mRNA. Known peptide sequences (such as avidin) might be used if biotin were the chosen 5' tag. In one example, a biotin ligase may be used to make covalent the interaction between the peptide and the biotin at the 5' end of the mRNA. See, Cronan, (Cell, 58:427, 1989); Reed and Cronan (J. Bio. Chem., 266:11425, 1991) incorporated herein by reference. Many suitable pairs of chemical adducts and fixed peptide sequences have been identified, and are known to those skilled in the art. For example, certain polypeptides contain lipoylation sites, and the post-translation modification would utilize the lipoylation system. See, Rucker et al., (FASEB J., 2:2252–61, 1988); Ali et al., (Mol. Microbiol. 4:943–50, 1990). For other post-translational modification systems, see, PCT Patent Application PCT/US90/02852 (published Nov. 29, 1990, WO 90/14431).

As the nascent peptide emerges from the ribosome, the most likely 5' adduct to be bound by that peptide sequence will be the 5' adduct on the mRNA encoding that exact peptide (which will include, in this case, randomized peptide sequences downstream of the fixed peptide adjacent to the initiating methionine). Again, with respect to biotin and biotin ligase, the first collisions will be irreversibly fixed. The length of the 5' end of each mRNA (that is, how many nucleotides upstream of the ribosome binding site are needed to enhance the binding reaction in cis) and the concentration of ribosomes that allow collisions between the nascent peptide of one ribosome and the 5' end of the mRNA of another can be determined easily without undue experimentation. This last point is clear from a simple calculation. Ribosomes are about 200 angstroms in diameter, so it may be assumed that the distance between the nascent, emergent peptide (from the large ribosome subunit) and the emergent 5' adduct of the mRNA (from the small ribosome subunit) will never be more than 500 angstroms apart and could be much less. The calculated concentration of the nascent peptide with respect to its own 5' adduct in cis is higher than 3 micromolar for a worst case scenario, and could be more than 100 times higher. Since the ribosome concentration in many cell-free translation experiments is sub-micromolar, it is not difficult to preclude scrambled binding between nascent peptides and 5' mRNA adducts on other ribosomes.

As translation ends, after mRNA polypeptide copolymer formation and prior to enrichment for peptides that partition with a target, the cell-free reaction may be treated with puromycin and EDTA to disassociate the ribosomal subunits. ATA, poly U, or other non-amplifiable RNAs may be added to prevent rebinding of mRNAs to the ribosomes. Size fractionation may then be used to enrich for small material, and/or high speed centrifugation would eliminate the ribosomes and many of the proteins from the cell-free system from the mRNA·polypeptide copolymer (such copolymers may be truly covalent or merely effective copolymers when very high affinities are used for the linkage). More complete purifications of the copolymer prior to partitioning with target are obvious. For example, hybridization to column-bound complementary DNA (to one end of the mRNA) and subsequent elution would give full purification. Similarly, the fixed peptide could include an additional sequence for this purification; a small epitope would do, thus allowing purification of the mRNA·polypeptide copolymer with antibodies against that epitope.

The mRNA·polypeptide copolymer is partitioned as in the ribosome complex examples, and the bound mRNA amplified via cDNA synthesis and PCR, as always extending the cDNA to create again the T7 promoter sequence for the next round of SPERT. The peptide attached to the 5' end of the mRNA may cause the 3' end of the cDNA to be a bit shorter than in the absence of peptide, but PCR easily accomplishes the full restructuring of the DNA for subsequent transcription, in this case initiated once again by phosphono monothioate nucleotide for adding the small organic molecule needed for linkage.

In this alternate embodiment of SPERT, the peptide is directly linked to the encoding nucleic acid and is partitioned to target (or reacted in any other way described for SPERT) with only the encoding nucleic acid available (along with the peptide collection) for that target. The very large ribosome or phage capsid no longer obscures the partitioning reaction in any way.

Activation of 5' end of mRNA and N-terminus of peptide.

The post-translational modification systems described above generally require an enzyme to facilitate the reaction between the nascent peptide and the mRNA. According to this embodiment, the modifying enzyme is eliminated, and relatively simple chemical reactions are relied on to form the copolymers.

In one embodiment of this system, sulfur-halide chemistry is employed. Sulfur may be incorporated on the 5' end of the mRNA using the T7 RNA polymerase and monothiate for initiation as described above. A halide can be incorporated on the N-terminus of the peptide by use of N-haloacetyl-met-tRNA$^{fmet}$ (Pellegrini et al., (Proc. Natl. Acad. Sci. USA, 69:83741, 1972); Sopari, et al., (Biochemistry, 13:5432–39, 1976)). This combination would result in spontaneous nucleophilic substitution to form a thioether linkage between the nascent polypeptide and the mRNA. In order to avoid reaction of the halo-acetyl group with DTT in the translation mixture, or with cysteine residues in ribosomal proteins, it is preferred that the chloro acetyl functionality be utilized.

In a further embodiment of this process, it may be desirable to accelerate the reaction between the nascent polypeptide and the mRNA by introducing a "chaperone" RNA sequence. The chaperone acts as a catalyst to facilitate the nucleophilic substitution reaction. An appropriate chaperone sequence may be easily selected by one skilled in the art utilizing the SELEX technology. A useful chaperone may be selected by placing a stretch of random noncoding RNA adjacent the 5' GMPS mRNA, and collecting those sequences capable of reacting with the halo-acetyl N-terminal polypeptide. This reaction could be further facilitated by selecting fixed amino acids at the N-terminal end that would present a probable nucleic acid interaction site. In further embodiments, the chaperone could be an RNA or protein acting as a true catalyst to facilitate the reaction.

Pre-coupling of mRNA to Peptide.

In one embodiment of the formation of mRNA·polypeptide copolymers, the mRNA may be coupled to the nascent polypeptide before translation is initiated. In one embodiment, this pre-translational coupling would occur by attaching the 5' end of the mRNA to the 60-amino group of methionine on met-tRNA$^{fmet}$ via a covalent linker. As translation proceeds, the initiating methionine is already attached to the mRNA at the initial amino acid sequence.

tRNA Crosslinking of Message and Peptide.

According to this embodiment, a covalent linkage is created between peptidyl-tRNA and mRNA. A specific embodiment of this system is based on studies of the photoreaction between the "Y" base of yeast tRNA$^{phe}$ and mRNA. See, Matzke et al., (Proc. Natl. Acad. Sci. USA, 77:5110–14, 1980). See also, Steiner et al., (Nucl. Acids. Res. 12:8181–91, 1984) (demonstration that tRNA can undergo peptidyl transfer and translocate normally from A-site to P-site after being crosslinked to mRNA); Paszyc et al. (Nucl. Acid. Reg. 6:385–97, 1979). A nonsense suppressor containing the Y base may be used that will crosslink to the message at the end of peptide synthesis, resulting in a peptide-tRNA-mRNA covalent complex. The peptide-tRNA linkage could be made into a stable amide linkage by making the 3' terminus of the tRNA 2'-deoxy-3'-amino-adenosine. See, Fraser et al. (Meth. Enzymol. 49:135–45, 1979).

Continuous irradiation of this system during translation would yield photocrosslinked mRNA·polypeptide copolymers. An advantage of this embodiment is that there would not be any constraints on the peptide or message.

It is an important and unexpected aspect of the present invention that the methods described herein can be employed to identify, isolate or produce polypeptide molecules which will bind specifically to any desired target molecule. Thus, the present methods can be employed to produce polypeptides specific for binding to a particular target.

Proteins contain within their primary sequence the information required to form an extraordinary variety of three dimensional shapes as is well known in the art. From this variety of potential shapes, along with the charge and/or hydrophobic qualities of amino acids, comes the potential for protein functions that are used in the biosphere. Proteins provide catalysis when embodied as enzymes; proteins can provide stable biological structures, for example, when used to construct spores, membranes, or viruses; and proteins can provide binding to a variety of targets, with appropriate affinities and kinetic parameters to allow life.

Nevertheless, this vast potential in chemical activities, including the extreme potential inherent in the mammalian immune system, has actually been explored rather narrowly by organisms. This fact can be noted with a simple calculation. If the average length of a protein is 300 amino acids, and if there are twenty natural amino acids used to construct modern proteins, the number of possible sequences of proteins of average size is $20^{300}$ or $\sim 10^{400}$. Estimates of the number of particles in the universe are in the range $10^{80}$, while estimates for the number of proteins ever explored in the entire history of the earth are in the range $10^{10}$. The tiny fraction of so-called sequence space that has been explored by biology is a result of evolutionary history and the relatively short age of the earth. The present invention provides the means to explore protein sequence space without historical and evolutionary limitations, while continuing to respect limitations established by the number of particles in the universe. The invention provides the means to identify and isolate polypeptide ligands with any desired quality from vast mixtures of protein sequences comprised largely of individual entities that have never before existed. The amino acid sequence of the selected ligand can be learned from the nucleotide sequence of its encoding mRNA, making tedious amino acid sequence determination unnecessary.

Even where the binding functions selected by SPERT have known naturally occurring counterparts, there is no reason to expect that the polypeptides selected by SPERT will resemble naturally-occurring proteins or peptides having similar function. In most instances, SPERT-selected polypeptides will be smaller than naturally-occurring proteins typically having a size of from 4–100 amino acids, preferably from 4–50 amino acids selected from randomized sequence of the same length, and also having a C-terminal trailer of about 30–40 amino acids and, optionally a N-terminal leader of about 10 amino acids, for a total length of about 100 amino acids, corresponding to a molecular weight of about 11 kd. This is smaller than most enzymes and all antibodies, for comparison, IgG has a molecular weight of about 150 kd. Furthermore, many polypeptide ligands of the invention will function when freed by N- and C- terminal trailers.

Therefore, the final product can be as small as 4–50 amino acids. The polypeptides of the invention are non-naturally-occurring, and typically differ in amino acid sequence and molecular size from naturally-occurring proteins. That portion of the amino acid sequence arising from randomized coding is designated the "binding segment" herein. The binding segment can be of any length, conveniently ranging from about 4–100 amino acids in length, preferably from about 15–50 amino acids in length. Additionally, given the vastness of sequence space, it is expected that most polypeptide ligands of the invention will have less than 50% homology with natural proteins, and preferably less than 30% amino acid homology with natural proteins.

A polypeptide ligand of the invention in a number of ways functionally resembles an antibody. Polypeptide ligands which have binding functions similar to those of antibodies can be isolated by the methods of the present invention. Such polypeptides are generally useful in applications in which polyclonal or monoclonal antibodies have found application. However, the polypeptide ligands of the invention have significant advantages over antibodies: they can be selected for any desired affinity, including higher affinities than are obtainable with antibodies, they can be selected to bind at any desired epitope or combination of epitopes, including binding sites not recognized by antibodies, they can be larger or smaller and have different solubility properties than antibodies and they can be generated by techniques that operate entirely in vitro, without the need for live animals or cell culture techniques. Applications of polypeptide ligands include the specific, qualitative or quantitative detection of target molecules from any source; purification of target molecules based on their specific binding to the polypeptide; and various therapeutic methods which rely on the specific direction of a toxin or other therapeutic agent to a specific target site. Target molecules are preferably proteins, but can also include among others carbohydrates, nucleic acids, peptidoglycans and a variety of small molecules. As with conventional antibodies, polypeptide ligands can be employed to target biological structures, such as cell surfaces or viruses, through specific interaction with a molecule that is an integral part of that biological structure. Polypeptide ligands are advantageous in that they are not limited by self tolerance, as are conventional antibodies. Also, as noted, polypeptide ligands of the invention do not require animals or cell cultures for synthesis or production, since SPERT is a wholly in vitro process. The methods of the present invention related to the use of polypeptide ligands can generate novel polypeptides that bind targets for which other proteinaceous ligands are known. For example, a number of proteins are known to function via binding to nucleic acid sequences, such as regulatory proteins which bind to nucleic acid operator sequences. The known ability of certain nucleic acid binding proteins to bind to their natural sites, for example, has been employed in the detection, quantitation, isolation and purification of such proteins. The methods of the present invention related to the use of polypeptide ligands can be used to make novel nucleic acid binding ligands having affinity for nucleic acid sequences which are known to bind proteins and to nucleic acid sequences not known to bind proteins. Novel, non-naturally-occurring polypeptides which bind to the same binding sites of nucleic acids can be developed using SPERT. As will be discussed below, certain polypeptides isolatable by SPERT can also be employed to affect the function, (for example inhibit, enhance or activate) specific target molecules or structures. Specifically, polypeptide ligands can be employed to inhibit, enhance or activate the function of proteins and of nucleic acids.

It is a second important aspect of the present invention that the methods described herein can be employed to identify, isolate or produce polypeptide molecules which will bind specifically to a particular target molecule and affect the function of that molecule. In this aspect, the target molecules are again preferably proteins or nucleic acids, but can also include, among others, carbohydrates and various small molecules to which specific polypeptide binding can be achieved. Polypeptide ligands that bind to small molecules can affect their function by sequestering them or by preventing them from interacting with their natural ligands. For example, the activity of an enzyme can be affected by a polypeptide ligand that binds the enzyme's substrate. Polypeptide ligands of small molecules are particularly useful as reagents for diagnostic tests, or other quantitative assays. For example, the presence of controlled substances, bound metabolites or abnormal quantities of normal metabolites can be detected and measured using polypeptide ligands of the invention. Antibodies to polypeptide ligands can be used to precipitate or bind ligand-target pairs to a solid phase matrix in a diagnostic assay. A polypeptide ligand having catalytic activity can affect the function of a small molecule by catalyzing a chemical change in the target. The range of possible catalytic activities is at least as broad as that displayed by natural proteins.

The strategy of selecting a ligand for a transition state analog of a desired reaction is one method by which catalytic polypeptide ligands can be selected. Polypeptide ligands with high affinity for transition-state analogues are likely to have enzymatic activity, as has been demonstrated for monoclonal antibodies directed against transition-state analogues. These antibodies have exhibited a wide range of catalytic activities, including acyl-transfer reactions [Pollack et al., Science 234:1570 (1986); Tramantano et al., Science 234:1570 (1986); Jacobs et al., J. Am. Chem. Soc. 109:2174 (1987); Napper et al., Science 237:1041 (1987); Janda et al., Science 241:1188 (1988); Schultz, P. G., Science 240:426 (1988); Benkovic et al., Proc. Natl. Acad. Sci. 85:5355 (1988)], carbon-carbon bond formation [Jackson et al., J. Am. Chem. Soc. 110:4841 (1988); Hilvert and Nared, J. Am. Chem. Soc. 110:5593 (1988)], carbon-carbon bond cleaving reactions [Cochran et al., J. Am. Chem. Soc. 110:7888 (1988)], peptide cleavage [Iverson and Lerner, Science 243:1184 (1989)], and ester bond hydrolysis [Janda et al., Science 244:437 (1989)]. The number of polypeptide sequences and structures that can be explored by SPERT far exceed those available in the immune system.

Enzymes are evolved using SPERT and starting randomized sequences corresponding to about 50 amino acids, as in Example 3. Enzymatic polypeptide ligands of small size are entirely unanticipated by the present understanding of enzymology; enzymes are always much larger in nature than the scientist expects. The specific transition state analogues used are drawn from the literature cited above. Among the reactions probed by the monoclonal antibody-enzymes are some which lead to the breakdown of toxic waste products, including chemicals with chlorine-carbon bonds and carbon-carbon bonds in ring structures like those found in benzene and polychlorinated phenols.

The binding selection methods of the present invention can be combined with secondary selection or screening to identify ligands capable of modifying target molecule function upon binding. The large population of variant amino acid sequences that can be tested by SPERT enhances the probability that polypeptide sequences can be found that have a desired binding capability and that function to modify target molecule activity. The methods of the present invention are useful for selecting polypeptide ligands which can selectively affect function of any target protein. The methods described herein can be employed to isolate or produce polypeptide ligands which bind to and modify the function of any protein or nucleic acid. It is contemplated that the method of the present invention can be employed to identify, isolate or produce polypeptide molecules which will affect catalytic activity of target enzymes, i.e., inhibit catalysis or modify substrate binding, affect the functionality of protein receptors, i.e., inhibit binding to receptors or modify the specificity of binding to receptors; affect the formation of protein multimers, i.e., disrupt quaternary structure of protein subunits; and modify transport properties of protein, i.e., disrupt transport of small molecules or ions by proteins.

Secondary selection methods that can be combined with SPERT include among others selections or screens for enzyme inhibition, alteration of substrate binding, loss of functionality, disruption of structure, etc. Those of ordinary skill in the art are able to select among various alternatives those selection or screening methods that are compatible with the methods described herein.

An embodiment of the present invention, which is particularly useful for identifying or isolating polypeptides which bind to a particular functional or active site in a protein, or other target molecule, employs a molecule known, or selected, for binding to a desired site within the target protein to direct the selection/amplification process to a subset of polypeptide ligands that bind at or near the desired site within the target molecule. In a simple example, a polypeptide sequence known to bind to a desired site in a target molecule is incorporated near the randomized region of all polypeptides being tested for binding. SPERT is then used to select those variants, all of which will contain the known binding sequence, which bind most strongly to the target molecule. A longer binding sequence, which is anticipated to either bind more strongly to the target molecule or more specifically to the target can thus be selected. The longer binding sequence can then be introduced near the randomized region of the polypeptide test mixture and the selection/amplification steps repeated to select an even longer binding sequence. Iteration of these steps (i.e., incorporation of selected sequence into test mixtures followed by selection/amplification for improved or more specific binding) can be repeated until a desired level of binding strength or specificity is achieved. This iterative "walking" procedure allows the selection of polypeptides highly specific for a particular target molecule or site within a target molecule. Another embodiment of such an iterative "walking" procedure, employs an "anchor" molecule which is not necessarily a polypeptide or amino acid. In this embodiment a molecule which binds to a desired target, for example a substrate or inhibitor of a target enzyme, is chemically modified such that it can be covalently linked to a bridge molecule which in turn is known to be bound to an oligopeptide of known sequence. The bridge molecule covalently linked to the "anchor" molecule that binds to the target also binds to the target molecule. The sequence encoding the known bridge-binding oligopeptide is incorporated near the randomized region of the test nucleic acid mixture. SPERT is then performed to select for those polypeptide sequences that bind most strongly to the target molecule/bridge/anchor complex. The iterative walking procedure can then be employed to select or produce longer and longer polypeptide molecules with enhanced strength of binding or specificity of binding to the target. The use of the "anchor" procedure is expected to allow more rapid isolation of polypeptide ligands that bind at or near a desired site within a target molecule. In particular, it is expected that the "anchor" method in combination with iterative "walking" procedures will result in polypeptides which are highly specific inhibitors of protein function.

In accordance with the teachings of copending applications Ser. No. 07/536,428 and Ser. No. 07/714,131, the translated mRNA of a ribosome complex or mRNA-polypeptide copolymer is, in principle, capable of binding to target molecules and of being partitioned concurrently with nascent polypeptides. In particular, where partitioning is accomplished by affinity chromatography, the selected ligand can be an RNA, rather than a polypeptide. Binding of mRNA can be differentiated from polypeptide binding once the ligand has been selected and both the selected polypeptide and its coding mRNA are available for independent direct binding studies where the two are not part of the same ribosome complex. Comparative studies of the relative frequency of RNA ligands and polypeptide ligands selected by SPERT are of fundamental biological importance to understanding the specialization of function that currently exists in living cells. This direct comparison between RNA and peptide during the SPERT cycles may prove to be surprisingly robust. As described in the SELEX applications, large numbers of protein targets will yield a tight-binding RNA ligand. For a given target it can not be predicted whether RNA or peptide will give more useful ligand solutions, and thus SPERT can be seen as an improvement to the SELEX application because when RNA yields the best ligand solutions the data will lead to that conclusion immediately. For example, the RNA ligand solutions will be indifferent to the reading frame in which the conserved RNA sequence or structure is found, while the peptide solutions will force the RNA solutions to have a common sequence in the same reading frame.

The polypeptides of the invention can be selected for other properties in addition to binding. For example, during partitioning, stability to certain conditions of the desired working environment of the end product can be included as a selection criterion. If a polypeptide which is stable in the presence of a certain protease is desired, that protease can be part of the buffer medium used during partitioning. As will be understood, when utilizing ribosome complexes conditions which disrupt ribosome complexes should be avoided. Other desired properties can be incorporated, directly into the polypeptide sequence as will be understood by those skilled in the art. For example, membrane affinity can be included as a property, either by employing a N- or C-terminal trailer having high hydrophobicity, or by biasing the randomized coding to favor the amino acids with lipophilic side chains.

The coding nucleic acid concomitantly selected by partitioning nascent polypeptides as described, is useful in its own right to transform host cells or organisms. The transformed organism is then useful for, e.g., fermentation production of the selected polypeptide. A transgenic organism can be rendered resistant to a virus infection, for example, by causing in vivo synthesis of a polypeptide ligand of the viral nucleic acid or a key viral protein. In principle, any functionality contributed by a polypeptide ligand of the invention can be bestowed on a suitable host organism. Methods known in the art can be used to combine the coding region with a promoter, polyadenylation signal functional in the intended host, followed by incorporation into a suitable vector for transformation, all as known and understood in the art.

EXAMPLES

The techniques and methods used in the ensuing examples are published and known in the art. Together with adaptations and modifications known to those of ordinary skill in the art, the procedures not specifically referenced herein are available from known reference works. In addition to Sambrook et al., (1989) supra, *Genetic Engineering*, Plenum Press, New York (1979); Weir, (ed.) (1986) *Handbook of Experimental Immunology in Four Volumes*, 4th Ed, Blackwell Scientific Publications, Oxford; and the multivolume *Methods in Enzymology* published by Academic Press, New York. Polymerase chain reaction techniques are described in PCR Protocols (Michael A. Innis, et al. eds.) (1990) Academic Press, Inc.

Throughout examples 1–9, reference is made to Tables 1 and 2. Table 1 lists oligonucleotide sequences used for preparing mRNA candidates. Table 2 lists the same sequences together with explanatory notes showing functional domains. Sequences in capitals are chemically synthesized, sequences in lower case letters are complementary sequences made enzymatically by DNA polymerase. The Examples could be adapted by those of ordinary skill in the art to generate mRNA·polypeptide copolymers as taught herein without undue experimentation.

Example 1

Direct Immunoprecipitation of Ribosome Complexes: Polypeptide Ligands Directed Toward Immunoglobulin Molecules.

Figure 1:
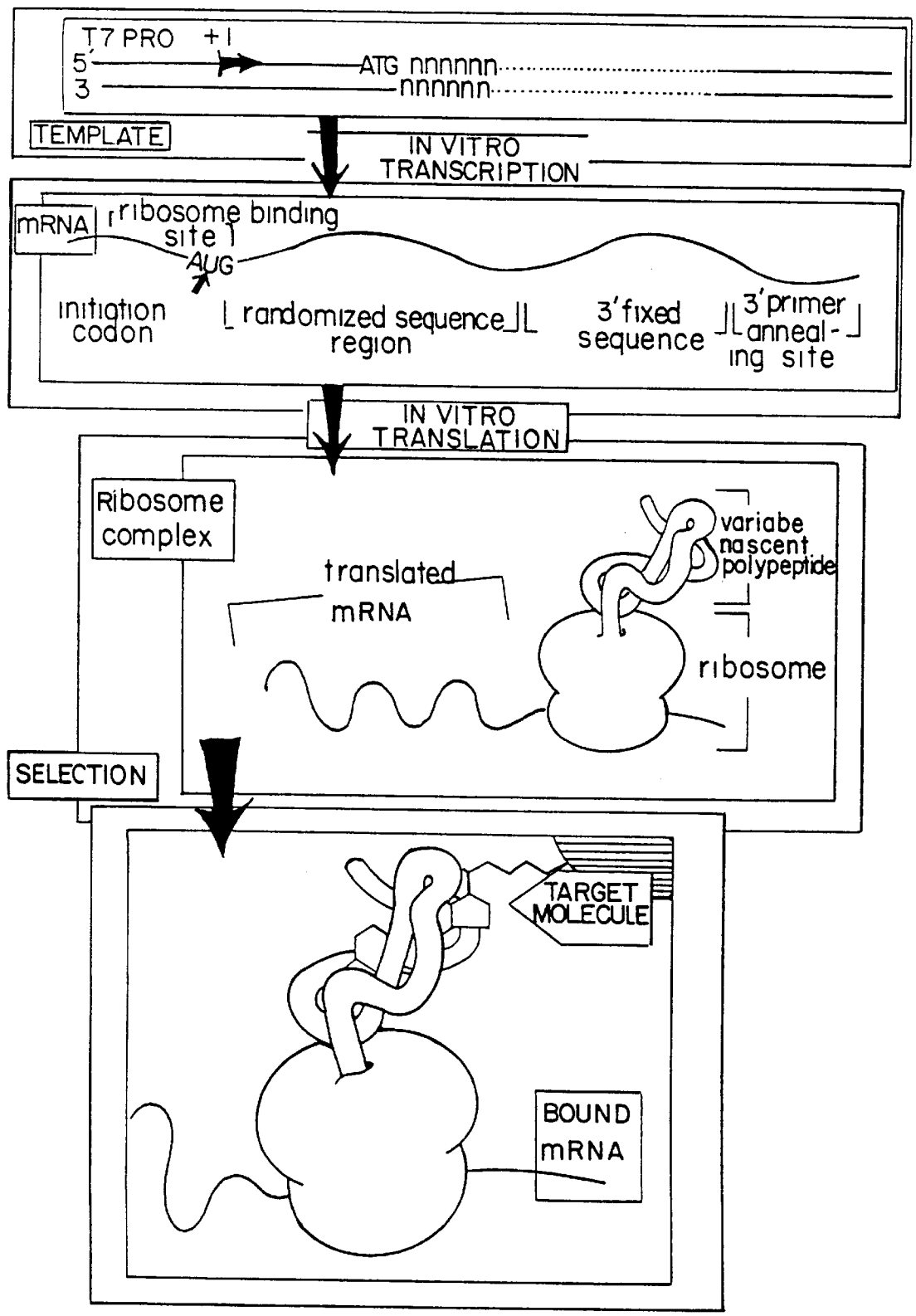
FIG. 1 is a diagrammatic representation of steps in the process of the invention. The top panel depicts a double-stranded DNA template having a T7 promoter ("T7 PRO") and a segment of randomized sequence, represented as "nnn . . . ", preceded by a start codon, ATG. The initiation site of transcription and direction of transcription are shown as a vertical line labeled "+1" and an arrow, respectively. In vitro transcription creates mRNAs (2nd panel) which contain, from left to right, a ribosome binding site, a randomized sequence region, a 3' fixed sequence region, and a 3' primer annealing site. In vitro translation of this mixture gives rise to ribosome complexes with randomized nascent polypeptides (3rd panel). The ribosome complexes are subjected to selection for affinity of the nascent polypeptide and a desired target molecule (bottom panel). The encoding mRNAs of the partitioned complexes are purified and subjected to amplification, e.g., by reverse transcription, PCR and transcription, to generate mRNAs for a second cycle of the process.
Figure 2:
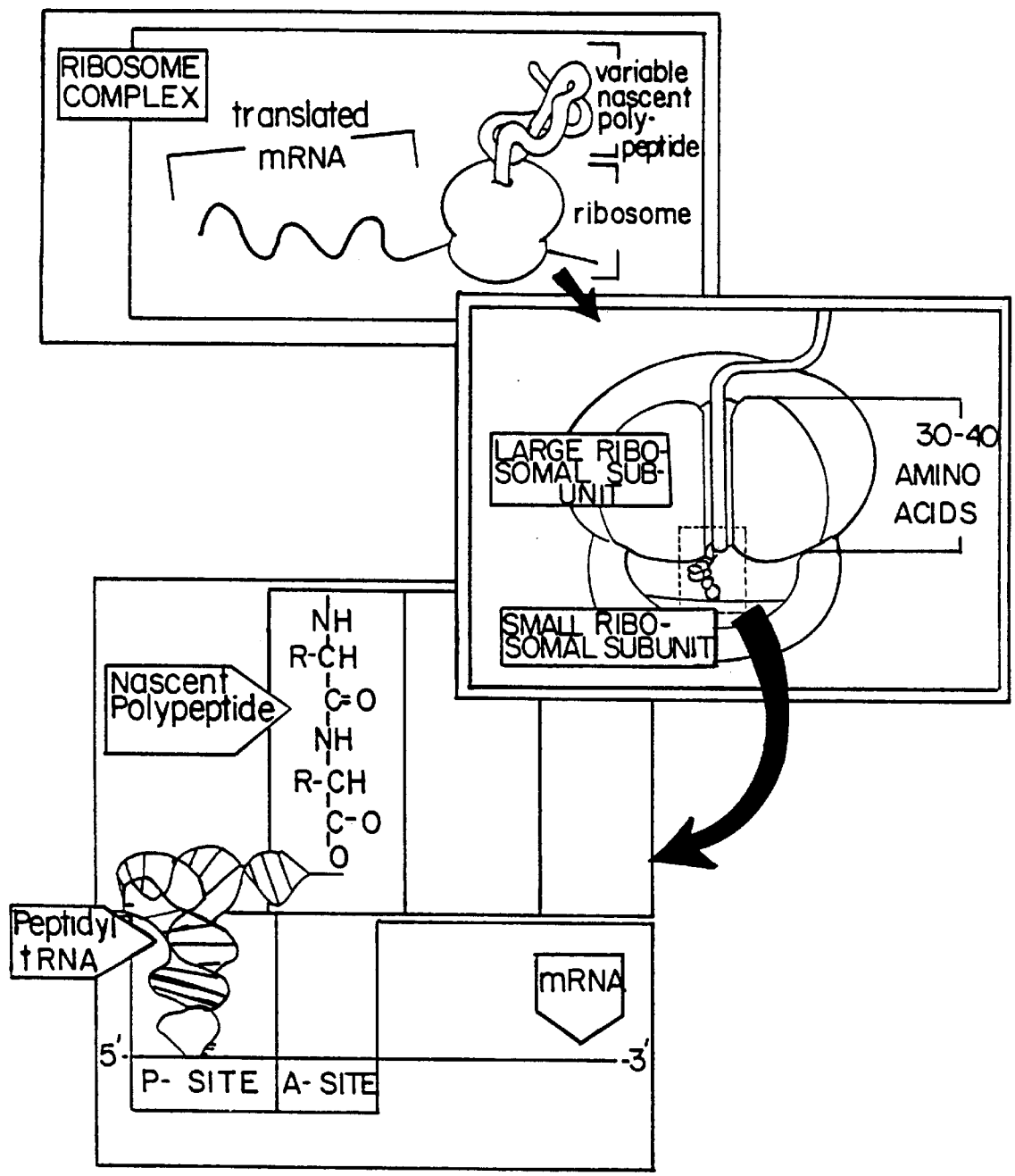
FIG. 2 is a diagram showing expanded views of a ribosome complex. The top panel is a ribosome complex as in the third panel of FIG. 1. A cut-away view of the ribosome (2nd panel) shows 30–40 amino acids of the nascent polypeptide buried in the complex and unavailable for interaction with the solvent. The ribosome is depicted with two shades of gray to indicate inner and outer regions. The nascent polypeptide is depicted as a thick white line extending vertically from a central tunnel (black) near the center of the ribosome. That portion inside the ribosome is depicted as 30–40 amino acids in length. The carboxy-terminal end of the nascent polypeptide is shown connected to a peptidyl-tRNA (curly black line). The region bordered by a dotted line is expanded in the bottom panel showing that the nascent polypeptide is covalently linked to a transfer RNA molecule which is hydrogen-bonded to the mRNA at a codon in the P-site.

The method of the invention is used to select novel polypeptides that bind the antibody of an epitope commonly recognized by the antisera from autoimmune mice which are the f1 progeny of a cross of NZB and NZW parents (Portanova et al., J. Immunol. 144, 4633 (1990). The known epitope consists of about 10 contiguous amino acids at the amino terminus of the histone H2B protein. To make mRNA encoding candidate polypeptides, a 5' fixed sequence composed of a T7 promoter sequence and a ribosome binding site which is recognized by both prokaryotic and eukaryotic ribosomes, terminating in a restriction endonuclease site is synthesized and cloned using oligonucleotides having the sequences shown as sequence 1 in Tables 1 and 2 and in FIG. 8. A 3' fixed sequence is placed into a restriction site to provide an mRNA encoding the C-terminal trailer sequence of ca. 100 nucleotides lacking stop codons (for ca. 30–35 amino acids) shown as sequence 3 in Tables 1 and 2 and FIG. 8. In addition, as shown in FIG. 1, a 3' primer annealing site (sequence 3) is provided so that cDNA synthesis can be accomplished on the mRNA recovered from partitioned ribosome complexes.

The randomized polypeptide insertion site is bounded by restriction endonuclease recognition sites, in this example EcoRI and PstI. A single-stranded oligonucleotide is synthesized with a randomized sequence of 45 nucleotides (corresponding to 15 codons) bounded by specific sequences that include those two restriction endonuclease sites (Sequence 4a). Synthesis of randomized oligonucleotides is carried out using an Applied Biosystems DNA synthesizer provided with a reactant mixture for each nucleotide position. To partially compensate for the amino acid sequence bias inherent in the redundancy of the genetic code, the reaction mixtures contain, on a mole percent basis, the following composition of bases for each codon: First position, C-20%, T, A, and G-30% each; Second position, C-15%, A-35%, T and G-25% each; Third position, T, C, A and G-25% each. Using a nucleic acid primer that is complementary to the fixed 3' end of the randomized oligonucleotide, randomized double-stranded DNA is created with the action of DNA polymerase. The products are digested with the two restriction endonucleases and ligated between the 5' fixed sequence and the 3' fixed sequence discussed above. In vitro transcription of these ligated templates using T7 RNA polymerase (Bethesda Research Laboratories, Gaithersburg, Md.) provides mRNA templates for in vitro translation. A rabbit reticulocyte lysate system (BRL) is used to translate the mRNA templates in vitro, using standard reaction conditions. Such translation of these transcripts results in a variety of ribosomal complexes (mRNA-nascent polypeptide-tRNA-ribosomes) that are identical except for the randomized region of the nascent polypeptide.

Figure 3:
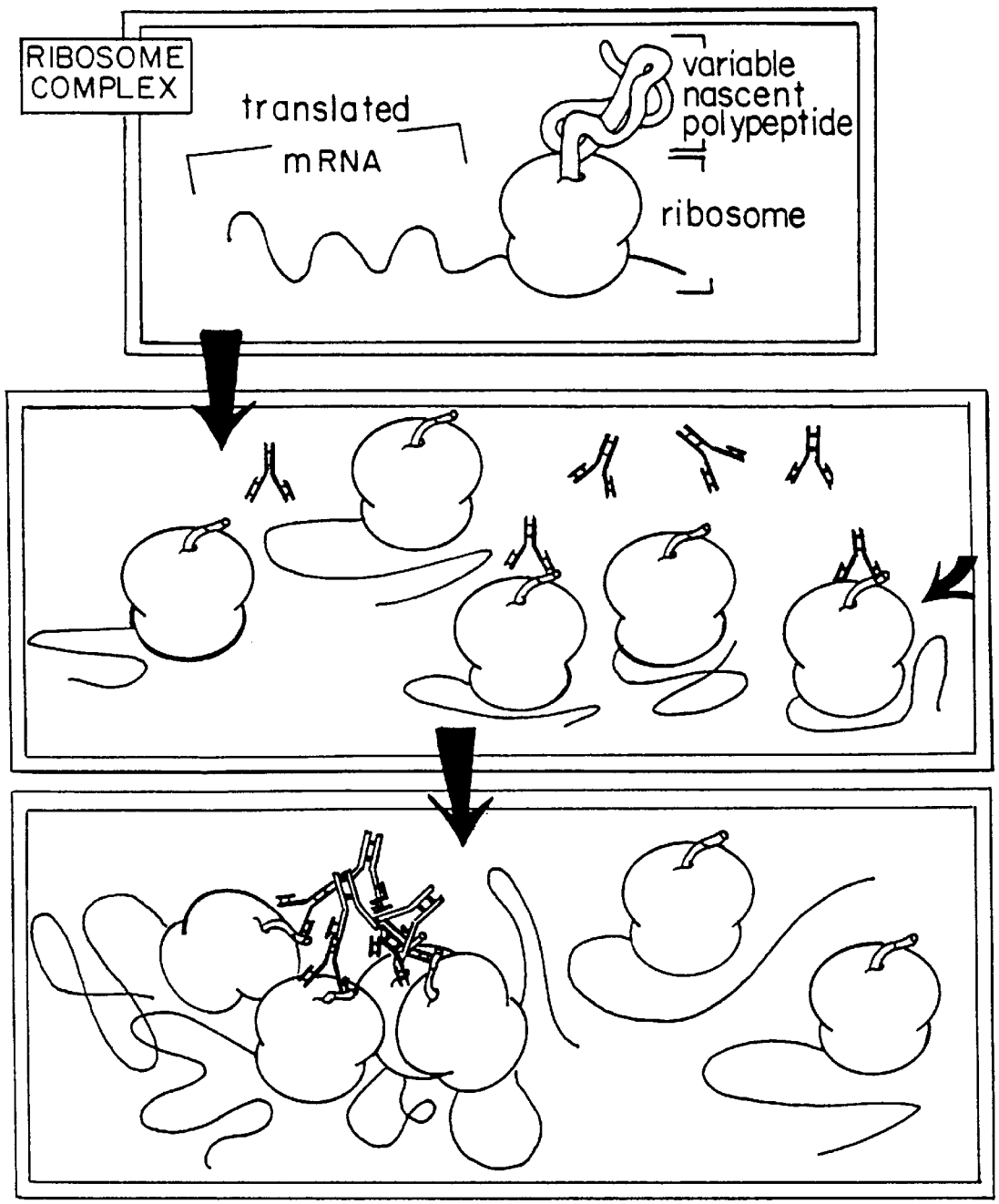
FIG. 3 is a diagram that represents partitioning polypeptide ligands by direct immunoprecipitation. The top panel is a ribosome complex as in FIG. 1. The center panel depicts several ribosome complexes where the nascent polypeptide is represented as a short, thick white line with hatching to indicate the segment of randomized sequence. Molecules of a first antibody (immunoglobulin) are represented as inverted Y-shaped structures drawn with heavy, straight black lines. Interaction (binding) of a nascent polypeptide with the epitope recognition site of an immunoglobulin is shown for two ribosome complexes. Nascent polypeptides are selected that have affinity for immunoglobulin molecules. The bottom panel shows addition of a second antibody (white inverted Y's) generally reactive to the first immunoglobulin resulting in an immunoprecipitate containing the selected ribosome complexes, shown as a cluster in the left half of the panel.

Antibodies (IgGs), Portamova et al., supra, which recognize the H2B histone epitope are added to the in vitro translation mixture. Immunoprecipitation of the immunoreactive ribosome complexes partitions the mRNAs species that encode the highest-affinity polypeptide ligands in the population (see FIGS. 3 and 4). Immunoprecipitated complexes are separated by low speed centrifugation. cDNA is synthesized from these mRNAs and is used via PCR to provide template for further cycles of transcription, translation, immunoselection and cDNA synthesis.

Clones are isolated as described in Application 07/536,428, Jun. 11, 1990, incorporated herein by reference. The individual polypeptide products are over-produced and purified and tested, using standard techniques for reactivity to the anti-H2B histone antibodies. In addition, the polypeptide ligands are challenged competitively with authentic histone H2B-derived epitomes to discover which polypeptide ligands bind to the same portion of the antibodies as the true epitope. Among the polypeptides isolated that bind the antibody are found those having less than 50% sequence homology with the H2B histone epitope. Other antibody binding sequences are identified having less than 30% homology with the H2B histone epitope. Other polypeptide ligands of the antibody do not compete for the H2B epitope binding site.

Example 2

Diagnostics Using the Polypeptide Ligands of Example 1: An Assay for Anti-H2B Antibodies in the Progeny of NZB×NZW Mice.

Auto-immune diseases result from the elaboration of an inappropriate antibody molecule with reactivity toward a normal cellular component (often a protein, but sometimes a nucleic acid, as in Systemic Lupus Erythematosis—SLE). Polypeptide ligands generated through the SPERT protocols in Example 1 are aimed at diagnosis of mouse "Lupus" in the offspring of NZB×NZW mice. SPERT is used to identify and obtain a reagent ligand for the diagnostic recognition of the auto-antibody that recognizes the histone H2B epitope.

As in Example 1, ribosome complexes are treated with the auto-antibody to partition reactive polypeptides from non-reactive polypeptides resident (as nascent polypeptides) in ribosome complexes. The auto-antibodies are used to precipitate the ribosome complexes containing polypeptides that fit into the active site of the antibody. The most avidly bound polypeptide emerges from repeated SPERT cycles.

The most avidly bound polypeptide ligand does not resemble in detail the epitope identified as the portion of the target that reacts with the antibody. Auto-immune diseases are triggered by unknown antigens, which are not necessarily the same as the target/epitope identified as the interactive species during the clinical stage of the auto-immune disease. For example, a virus infection may trigger an immune reaction that yields a class of antibodies that cross-react with a normal cellular target. Such antibodies may bind more avidly to the original, stimulatory, viral antigen than to the epitope on the cellular target. As another example, the epitope on the cellular target may not take full advantage of the binding site on the antibody.

The polypeptide ligand is used diagnostically to measure the quantity of circulating auto-antibody, using, e.g., an ELISA assay. The technology is available to one skilled in the art, without undue experimentation. As another example, the fixed portion of the polypeptide ligand is used as the reporter substance when the polypeptide ligand interacts with the circulating auto-antibody. With a fixed carboxy-terminus of beta-galactosidase or alkaline phosphatase, serum protein samples attached to plastic plates are assayed directly for the anti-H2B antibody by "staining" with the polypeptide ligand covalently fused (by recombinant DNA techniques) to either reporter enzyme.

Example 3

Indirect Immunoprecipitation: Polypeptide Ligands Directed Toward Domains of any Protein.

Immunization of animals with antigens, whether crudely prepared or purified, often results in immune responses directed at a subset of the available epitomes in that antigen. The polyclonal sera may react largely with a single protein domain in that antigen. Similarly, when researchers attempt to raise antibodies against fusion proteins, often the well-known fusion partner is immuno-dominant over the new protein portion of the fusion.

Antibodies aimed at a protein target (but that do not recognize the portion of the target that one wishes to use as the target in SPERT) allow INDIRECT Immunoprecipitation of ribosome complexes. That is, immunoprecipitation is a useful partitioning step when antibodies are aimed at domains in the target that are different from those domains pre-selected for SPERT-based ligand evolution. This protocol is sometimes called "panhandling", and can yield high-affinity polypeptide ligands for target domains that are weakly immunogenic.

SPERT is performed using variable material prepared as in Example 1 except that the randomized mRNA regions are now set to yield about 50 amino acids in the solvent-exposed nascent polypeptide. Biased randomization is done so that chain termination codons are not likely over the 150 randomized nucleotides; in addition, cell-free translation is performed in the presence of so-called suppressor tRNAs so that translation continues to the desired portion of the mRNAs.

The population of ribosome complexes is pre-treated with the antisera aimed at the target protein, but in the absence of that target protein. The pre-treatment is designed to eliminate any nascent polypeptides that react directly with the antibodies, as in Example 1. The target protein is then added to the ribosome complexes, along with antibodies aimed at the target protein. Partitioning occurs as the ribosome complexes that interact with the target at the same time (see FIG. 4).

The single-stranded DNA binding protein of bacteriophage T4 (gp32) has an acidic carboxyterminal region which is immunodominant (K. Krassa, Ph.D., Thesis, 1987). In one immunization experiment, polyclonal sera react exclusively with the carboxyterminal domain of the protein; 12 monoclonal cell lines derived from hybridoma fusions with spleen cells from such immunized animals produced antibodies that react with the same target domain. Purified polyclonal sera which react with the carboxy-terminal domain of gp32 are used for indirect immunoprecipitation in this example.

A population of ribosome complexes is produced (above). These ribosome complexes are pre-treated with the polyclonal sera aimed at gp32; this is readily accomplished by passing the ribosome complexes through Staph A columns pre-bound with the polyclonal sera against gp32. Subsequently, those ribosome complexes unable to react directly with antibodies raised against gp32 are reacted with gp32, followed by treatment with the sera aimed at the carboxy-terminus of gp32. Goat anti-mouse antibodies are used to immunoprecipitate gp32 and whatever ribosomal complexes interact with the core domain of gp32. Cycles of SPERT are continued until a desired level of binding is attained. Sequences are then cloned and individuals identified and tested for affinity to gp32.

Example 4

Isolation of a Polypeptide Ligand for a Serine Protease.

Serine proteases are protein enzymes that catalyze hydrolysis of peptide bonds within proteins, often with high selectivity for specific protein targets (and, of course, for specific peptide bonds within the target protein). The serine proteases are members of a gene family in mammals. Examples of serine proteases are tissue plasminogen activator, trypsin, elastase, chymotrypsin, thrombin, and plasmin. Many disease states can be treated with polypeptide ligands that bind to serine proteases, for example, disorders of blood clotting. Elastase inhibitors are likely to be useful in minimizing the clinical progression of emphysema. Proteases other than serine proteases are also important in mammalian biology, and these too are targets for polypeptide ligands with appropriate affinities obtained according to the invention herein taught.

A ligand that binds to porcine elastase is identified and purified using the starting randomized material of Example 3. Serine proteases are easily attached by standard methods to column support materials with retention of enzymatic activity. Porcine elastase attached to agarose is available from commercial sources. Thus, in this example affinity chromatography is the partitioning method. Natural elastase inhibitors are available, and are used to check that the active site of the bound elastase is available for the binding of an inhibitory ligand. The buffer used for binding during the SPERT cycles must not denature or otherwise inactivate elastase; dithiothreitol, which can reduce protein disulfide bonds, is left out of the binding buffer.

After several rounds of SPERT, as the affinity of the mixture of nascent polypeptides becomes high, a reversal of the elution parameters is used. Early rounds of SPERT are aimed at obtaining any polypeptide ligand that binds to any domain of elastase; after virtually all the nascent polypeptides are able to bind the column, the ribosome complexes are poured through a column that has been pre-saturated with a natural inhibitory ligand for the elastase active site. In addition, the elution buffer for this procedure includes high concentrations of that same natural inhibitory ligand. The ribosome complexes that are not bound in this reversed elution procedure are used to prepare mRNAs for further SPERT cycles, once again depending on high affinity for the bound elastase. This procedure focuses the evolving polypeptide ligands toward the elastase active site.

When the mixture of polypeptide ligands has a high affinity for the bound elastase, and is aimed primarily toward the active site, further enrichment for high affinity inhibitors of elastase activity is accomplished by including low concentrations of the natural inhibitors in the partitioning steps, thus demanding that the evolving polypeptide ligands have higher affinity than the effective affinity of the natural inhibitor at the concentration used.

Nucleic acids encoding polypeptide ligands are cloned and sequenced, and binding affinities and inhibitory binding affinities for elastase are measured. Binding affinities and inhibitory efficiencies are measured with the same polypeptide ligands for other members of the serine protease family in order to ascertain specificity within the family.

Example 5

Polypeptide Ligands that Antagonize a Receptor: A Synthetic Inhibitor of the Interleukin-1 Receptor.

Receptors are a class of proteins that are partially integrated into the cell's cytoplasmic membrane such that a domain resides outside the cell. That domain serves as a binding site for cell extrinsic molecules, including growth factors, peptide hormones, non-peptide organic molecules (which may include hormones), or even ions. Receptors handle the bound ligand in several different ways, including signal transduction through the membrane or internalization of the bound ligand for its subsequent function. In either case polypeptide ligands of the invention may be used to affect function of the receptor, that is to cause the normal activity of the natural ligand or to block that activity.

Receptor antagonism for a useful therapeutic purpose is accomplished by generating a polypeptide ligand through SPERT that is aimed at the interleukin-1 (IL-1) receptor. A natural antagonist of the receptor has been found (Hannum et al., Nature, 343:336–340 (1990); Eisenberg et al., Nature, 343:341–346 (1990), and that antagonist has the presumptive utility of preventing or easing inflammatory problems such as those found in rheumatoid arthritis. The natural antagonist (called IL-1ra for IL-1 receptor antagonist) is partially homologous to IL-1 itself, and is a competitive inhibitor of interleukin-1 binding to the receptor. The natural IL-1ra is a pure antagonist, completely without agonist activity at the highest concentrations used in the work cited above. IL-1ra is synthesized as a protein with 177 amino acids; after post-translational cleavage the active inhibitor has 152 amino acids and, additionally, is glycosylated. However, the activity of recombinant IL-1ra, without glycosylation, is comparable to the activity of the natural inhibitor.

SPERT is used to develop a polypeptide ligand antagonist for the interleukin-l receptor. Two methods are used. In the first monoclonal antibodies are raised against interleukin-1 that are able to cross-react with IL-1ra. Such monoclonal antibodies in principle recognize the features in common between IL-1 and IL-1ra. Those monoclonal antibodies are used, as in Example 1, to develop polypeptide ligands that bind to the antigen combining site; such polypeptide ligands are candidates for a novel class of IL-1 antagonists. Since one goal in this case is to provide antagonists smaller than the natural IL-1ra, the randomized polypeptide is ca. 50 amino acids, as in Example 3.

In a second methodology the extracellular domain of the IL-1 receptor is itself used as the target for polypeptide ligand development through SPERT. The domain is attached to an insoluble matrix. Candidate polypeptide ligands, residing in ribosome complexes, are partitioned on the matrix. The matrix is eluted with high concentrations of IL-1, thus displacing the ribosome complexes and nascent polypeptides with the natural ligand known to bind to the desired active site on the receptor. Cycles of SPERT are continued until high affinity polypeptide ligands are identified.

Very high affinity, even covalent, antagonists of the receptor are isolated by an elution protocol during SPERT that denatures the ribosome complexes even if the polypeptide ligand remains strongly bound to the receptor. The mRNA eluted from the column under protein denaturing conditions is used to prepare cDNA which is amplified through PCR, after which transcription provides mRNA for the next round of SPERT.

All genes encoding polypeptide ligands are sequenced, and the polypeptide ligands are tested for IL-1 receptor antagonism. Those ligands identified by receptor-based affinity chromatography are tested with the antibodies of the first method to screen for the novel antagonists recognized by those antibodies that recognize structural or sequence homology between IL-1 and IL-1ra. Novel, SPERT-generated polypeptide ligands having IL-1 receptor antagonist activity are isolated and characterized. SPERT-generated antagonists having less than 50% amino acid homology with natural IL-1ra are identified. In addition, SPERT-generated antagonists having less than 30% amino acid homology are identified.

Example 6

Protein Improvement by SPERT: Mutagenesis and Selection of Better Natural Insecticides.

Bacillus thuringiensis is a gram-positive, spore-forming bacteria which produces insecticidal proteins. These proteins, derived from different B. thuringiensis strains, have varying effectiveness for killing insect larvae of different species. Although one specific protein will kill the insect larvae of a variety of species, the effectiveness toward the different insect targets (measured as the level of protein required to produce 50% mortality) can vary by as much as 2000-fold. The mechanism of action for these insecticide proteins is to bind a receptor on the gut membranes of the susceptible insect larva. Such membranes serve as a functional partitioning tool in SPERT.

We create double-stranded DNA templates suitable for SPERT by PCR; the appropriate DNA encodes the N-terminal 646 amino acid portion of the insecticidal protein from t. subspecies kurstaki HD-1, which is fully active (Fischhoff et al., Biotechnology 5:807–813 (1987). This protein kills the larva of tomato hornworm and cabbage looper very effectively at low concentration. Substantially more protein is required to kill tobacco budworm, corn earworm, black cutworm, European cornborer, and beet armyworm. Gut membranes from each of these insect larvae will be used as partitioning agents in SPERT.

The starting material in these experiments is RNA derived from the cloned gene, as above. Two methods are used to create protein variants. In one method mutagenic PCR provides random mutations throughout the 646 amino acids of the insecticide. In fixed codons within the insecticide, using about 50 amino acid replacements. In particular, randomized DNA is used to replace the codons encoding the hypervariable region of the Bt. toxin. Rounds of SPERT are continued until a desired level of binding to gut membranes is achieved. The DNA products are cloned and sequenced and individually assayed for effectiveness in binding membranes and larval killing. Effective toxins are selected by SPERT, having a naturally-occurring sequence replaced by a sequence that is less than 50% homologous with the replaced sequence. In addition, toxic, SPERT-generated variants are identified wherein the original, naturally-occurring sequence is replaced by a sequence having less than 30% sequence homology with the replaced sequence.

Example 7

Anti-viral Polypeptide Ligands: Inhibition of Viral Entry into Target Cells.

Receptors are often used for viral attach on cells. Recently Kaner et al. (Science, 248:1410–1413 (1990)) described the basic fibroblast growth factor (FGF) receptor as the likely portal through which Herpes Simplex Virus Type 1 (HSV) enters a cell. In that same paper, by citation of other work several other viruses are said to utilize other receptors to gain cellular entry. Rhinovirus, the common cold virus, is said to enter cells through a cell adhesion molecule ICAM-1. HIV, the AIDS virus, enters cells through the CD4 glycoprotein receptor. Epstein-Barr virus enters T lymphocytes via the C3d complement receptor. Rabies virus enters nerve cells through the acetylcholine receptor. Reovirus enters cells through the beta-adrenergic receptor. Vaccinia virus enters cells through a functional interaction with the epidermal growth factor receptor. Apparently viruses survive in part by using absolutely crucial cell receptors to gain entry into susceptible hosts. That is, host organisms can not easily alter such important receptors so as to become resistant to the virus without suffering some impairment of crucial cell and organism functions.

Polypeptide ligands of the invention are identified that diminish viral uptake through receptors while still allowing critical growth factors to function. The basic FGF receptor is used to demonstrate a successful strategy. The soluble domain of the basic FGF receptor (Lee et al., Science, 245:57 (1989)) is used as the target. A candidate mixture of polypeptide ligands is used as in Example 3. The partitioning of ribosome complexes is obtained with matrix bound extracellular domain of the FGF receptor. The cycles of SPERT are altered to include an elution step from the matrix with high concentrations of HSV; during this elution step the ribosome complexes that exit the column are discarded, while those ribosome complexes that remain on the column are further eluted with high concentrations of FGF itself. Those ribosome complexes that are not displaced by HSV but are displaced by FGF contain nascent polypeptides that are candidate ligands with the desired specificity. Such polypeptides bind FGF receptors in a way that inhibits HSV binding but does not interfere with FGF binding. Several cycles of SPERT are used to find the most avidly bound polypeptide that is eluted with FGF but not with HSV. Candidate polypeptides are assayed for their negative impact on HSV infection and their inability to prevent FGF-mediated cell growth. The most useful polypeptide ligands in this example are neither antagonists nor agonists of the FGF receptor at concentrations that diminish HSV infection. Novel polypeptides meeting these criteria are made using the process as described. A polypeptide meeting the criteria having less than 50% amino acid homology with FGF is isolated. In addition, a polypeptide meeting the criteria having less than 30% homology with FGF is isolated.

Example 8

Polypeptide Ligands That Enter Cells: The Glucocorticoid Receptor and Trojan Horse Ligands.

The glucocorticoid receptor protein binds steroid hormone, after which the receptor protein is internalized from the membrane so that the receptor can make its way into the cell nucleus. The receptor has a DNA binding domain (DBD) that interacts in the nucleus with target DNA sequences. Polypeptide ligands of the invention, agonists of the glucocorticoid receptor, are internalized along with the receptor, and thus directed sequentially to the cytoplasm and then to the nucleus. Depending on the dissociation rate constant for specific polypeptide ligands, these ligands largely reside after uptake in either the cytoplasm or the nucleus.

Using the randomized starting material of Example 3, SPERT is directed toward the glucocorticoid receptor, either with indirect immunoprecipitation or affinity chromatography using bound receptor. As in prior example, SPERT protocols are manipulated so that polypeptides are found that compete directly for the glucocorticoid binding domain but that have much lower affinity than that observed for steroid hormones. As the polypeptide ligands evolve, screening of potential ligands is performed on individual candidates; thus resistance to proteolysis of the polypeptide ligand is tested using whole cell entry prior to the protease challenge, and testing both cells with and without an abundance of the glucocorticoid receptor. Polypeptide ligands that enter cells are localized in the cytoplasm or nucleus by means available to those skilled in the art. Those polypeptide ligands that enter cells with proper localization are fused to other polypeptide ligands to provide cell entry for molecules with other useful activities.

Example 9

Polypeptide Ligands Toward Nucleic Acids: Inhibitors of Transcription.

Cancer cells can result from the over-expression of a transcriptional activator protein that functions to enhance transcription and subsequent expression of sets of genes that push the cell toward inappropriate and uncontrolled growth. Thus, mutations that elevate the activity of a transcriptional enhancer may cause cancer through enhancement of the expression of a set of genes relevant for growth control. Such tumors are treatable with polypeptide ligands that reset the appropriate level of expression or activity of the transcriptional enhancer. While it is likely that polypeptide ligands may be aimed at the enhancer protein directly, thus inhibiting the activity and resetting a proper growth rate, in the present example a polypeptide ligand is aimed at the production rate of the transcriptional enhancer.

The polypeptide ligand of interest binds to the genome of the cancer cell at a location that competes for transcription of the gene that encodes the transcriptional activator protein, and hence expression of that protein. That is, in classical genetic language, the polypeptide ligand is a specific transcriptional repressor.

The starting materials of Example 3 are used to generate a mixed pool of candidate polypeptides. A specific sequence of double-stranded DNA is prepared by chemical means and covalently attached to an insoluble column matrix. The column matrix is chosen such that ribosome complexes in general are able to flow through the column containing bound DNA. Ribosome complexes containing nascent polypeptide ligands that interact with double-stranded DNA (either with sequence specificity or not) are retarded on the column, recovered, and placed into the SPERT protocol of mRNA-amplification, transcription, and a second cycle. In order to eliminate polypeptide ligands with affinity for all double-stranded DNA (that is, without adequate sequence specificity for the intended use), the ribosome complexes are mixed with random soluble double-stranded DNA sequences prior to the column partitioning step. The soluble DNA concentration is adjusted to give about tenfold more non-specific DNA during the partitioning step than is the abundance of specific DNA sequences attached to the column. In this manner polypeptide ligands that are indifferent to DNA sequence emerge from the column along with ribosome complexes containing polypeptide ligands that are unable to bind DNA at all.

Polypeptide ligands aimed at a specific DNA sequence are characterized further. Randomized DNA sequences are used to establish which nucleotide pairs in the covalently attached DNA are required for avid binding of the polypeptide (using the SELEX protocol described in U.S. Pat. Ser. No. 07/536,428). A second SPERT is directed toward the contiguous DNA base pairs that are not bound by the first isolated polypeptide ligand, and the genes for the first and second polypeptide ligands are combined to yield a polypeptide ligand fusion (in either order, and containing a flexible peptide linker) to provide a polypeptide ligand with higher specificity and avidity than is available from either polypeptide ligand by itself. This improvement in specificity and avidity is an example of walking, although in this case the "steps" are made independently and the polypeptide ligands joined post-identification.

The sequence of double-stranded DNA chosen in this example must overlap a transcriptional initiation signal. The ras oncogene transcriptional initiation region is chosen first.

Example 10

Human c-myc Protein Epitope.

This experiment shows that it is feasible to select an epitope or epitopes from a random mixture of RNA-encoded peptides. An antibody was chosen which recognizes an epitope in human c-myc protein consisting of the amino acid sequence Glu-Gln-Lys-Iso-Ser-Glu-Glu-Asp-Lys (SEQ ID NO:1) (described in Evan et al., Mol. Cell. Biol. 5, 3610–3616, 1985). An expression system may be set up for conducting SPERT experiments utilizing a T7 promoter, a 5' untranslated region (5'-UTR) containing signals for either eukaryotic or prokaryotic translational initiation, insertion sites for random or non-random sequences which would encode nascent peptides accessible to selection on ribosomes, and a 3' fixed translated sequence (3'-FTR) which encodes peptide sequences which are buried in the translating ribosome. Refer to Table 3. The T7 promoter sequence was added to the eukaryotic 5' UTR through PCR with oligos 1 and 2 from Table 3 using plasmid pSPBP4 which is described by Siegel and Walter, (Cell 52: 39–49, 1988). The 3'-FTR was obtained by PCR of the same plasmid using oligos 9 and 10 from Table 3. These two fragments, 5'-UTR and 3'-FTR were cut with NheI and ligated. The ligated fragment was purified and further PCRd prior to cloning into the HindIII and BamHI sites of pBSSK+ (purchased from Strategene Systems, Inc.) to create the plasmid pPSX-EUK. The prokaryotic 5'-UTR will be cloned using oligos 3 and 4 from Table 3 into the HindIII and Nhe I site of pPSX-EUK to create pPSX-PROK replacing the eurkaryotic ribosome binding site with a prokarytic one. The myc epitope encoding insert is obtained by PCRing the template oligo 7 with the oligos 5 and 6, all from Table 3, and the variable insert (for eight amino acids) is obtained by PCRing the template oligo 8 with the oligos 5 and 6, from Table 3. These inserts will be digested with NheI and EcoRI and ligated in the presence of likewise digested pPSX-EUK and pPSX-PROK. (This was done for the myc insert in pPSX-EUK). Thus there will be a positive control myc epitope-encoding expression system which can be translated by eukaryotic translation systems and separately by prokaryotic translation systems, and variable nascent peptide-encoding system which can be likewise variably translated, and a system with no inserts which can serve as an internal control for comparing extents of enrichments by selection of polysomes by the anti-myc antibody. Further testing will identify what 3' ends will give the stablest polysome complexes; this may be accomplished by using oligos 10 in PCR (with oligo 1) to create multiple histidine codons for translation with no added histidine, with oligo 11 for normal unstopped translation with no amino acid depletion, and to test the extent of translation using oligo 12 which puts two stop codons allowing repeated translation of individual mRNAs.

TABLE 1

1.) 5'-CCGAAGCTTAATACGACTCACTATAGGGCGACATACATTTACACACATAA-3' (SEQ ID NO. 2)
2.) 5'-CGGGAATTCTTTCATATTATATTTCCTCCTTATGTGTGTAAATGTATG-3' (SEQ ID NO. 3)
3.) 5'-GGCGAATTCTGCTGCTGCAGTGCTGCCATGGTTGCGACGGTCAGGA-3' (SEQ ID NO. 4)
4.) 5'-CCGCCGGATCCTCCTGTCCGTCGCAA-3' (SEQ ID NO. 5)
5.) 5'-CCCGAATTC-[-45N-]-CTGCAGTGCTGCCATGGT-3' (SEQ ID NO. 6)
6.) 5'-ACCATGGCAGCACTG-3' (SEQ ID NO. 7)
7.) 5'-GGGCCATGG-[-120(ACG)-]-CCATGGTTGCGATGGTCAGGA-3' (SEQ ID NO. 8)
8.) 5'-TCCTGTCCATCGCAA-3' (SEQ ID NO. 9)

TABLE 2

1.) 5' fixed sequence

HindIII site                +1                Ribosome binding site      EcoRI
5'-CCGAAGCTTAATACGACTCACTATAGGGCGACATACATTTACACACATAAggaggaaauauaaauatgaaagaattcccg –3' (SEQ TABLE 2-continued 3'-ggcttcgaattatgctgagtgatatcccgct GTATGTAAATGTGTGTATTCCTCCTTTATATTATACTTTCTTAAGGGC-5' ID NO. 10)
   — T7 promoter —

2.) Stratagene polylinker cloning site (pBSSK+)

PstI
            5'-TCGATAAGCTTGATATCGAATTCCTGCAGCCCGGGGGATCCACTAG-3' (SEQ ID NO. 11)
                        ------    ------              ------
                        HindIII   EcoRI               BamHI 3.) 3' primer annealing site and insertion sequence cloning sites EcoRI        PstI         NcoI              BamHI
            5'-GGCGAATTCTGCTGCTGCAGTGCTGCCATGGTTGCGACGGTCAGGAggatccggcgg-3' (SEQ ID NO. 12)
            3'-ccgcttaagacgacgacgtcacgacggtaccAACGCTGCCTGTCCTCCTAGGCCGCC-5'

4.) Randomizing oligonucleotides to be cloned at the EcoRI, PstI, and NcoI sites EcoRI           PstI
   a.)   5'-CCCGAATTC-[-4-5N-]-CTGCAGTGCTGCCATGGT-3' (SEQ ID NO. 6)
                              3'-GTCACGACGGTACCA-5'

NcoI           NcoI
   b.)   5'-GGGCCATGG-[-120(ACG)-]-CCATGGTTGCGATGGTCAGGA-3' (SEQ ID NO. 8)
                                  3'-AACGCTACCTGTCCT-5'

TABLE 3

5' UTR

*********************************************************************************

1. PE5 (5' primer for 5' untranslated region (UTR) and full-length PCR)

5'-GGGAAGCTTAATACGACTCACTATAGGGAGCTTGTTCTTTTTGCAGAAGCTCAG-3' (SEQ ID NO. 13)

*********************************************************************************

2. 3' (3' Primer for PCRing the 5' untranslated region prior to ligation)

5'-CTCGGCGCTAGCCATGGTGATTGCCAAAGTTGAG-3' (SEQ ID NO. 14)

*********************************************************************************

3. PROTOP (5' primer for fixed proke UTR-RBS PCR and cloning)

5'-CCGAAGCTTAATACGACTCACTATAGGGTAAGATAAGATAAGGAGGAAAATAAAATGG-3' (SEQ ID NO. 15)

*********************************************************************************

4. PROBOT (Complement to Protop for cloning proke UTR-RBS)

5'-CTAGCCATTTTATTTTCCTCCTTATCTTATCTTACCCTATAGTGAGTCGTATTAAGCTTCGG-3' (SEQ ID NO. 16)

*********************************************************************************

Insert

*********************************************************************************

5. 5' ertPrimer (for amplifying insert)

5'-GGGCCATGGCTAGCGCCGAGGA-3' (SEQ ID NO. 17)

*********************************************************************************

6. PM3 (3' primer for fixed epitope (EPI) and variable region (VAR) PCR, sequencing and (maybe) cloning)

5'-GGCGGATCCAGGCGGGACCCTTTCTGCGACGAA-3' (SEQ ID NO. 18)

TABLE 3-continued

7. MycCODE (oligo for EPI construction)

5'-GGGCCATGGCTAGCGCCGAGGAGCAGAAGCTGATCTCCGAGGAGGACCTGCTGGAATTCGTCGCAGAAAGGGTCCCG-3' (SEQ ID NO. 19)

8. VarCODE (oligo for VAR construction)

5'-GGGCCATGGCTAGCGCCGAGGAGNNNNNNNNNNNNNNNNNNNNNNNNNCTGCTGGAATTCGTCGCAGAAAGGGTCCCG-3' (SEQ ID NO. 20)

Fixed translated region

9. PM5 (5' primer for 3' Fixed Translated region (FTR) PCR)

5'-GGGCCATGGCTAGCGCCGAGCTCGAATTCAGCAAAGGTTCGTCGCAGAAAGGGT-3' (SEQ ID NO. 21)

10. HisPrimer (3' primer for 3' FTR to test His minus translation.)

5'-CCCGGATCCGTGTGTGTGTGTGCATGACTGCCCGGTCAAACAGGTC-3' (SEQ ID NO. 22)

11. PE3 (3' primer for 3' FTR (truncated stop) and full-length PCR)

5'-CCCGGATCCATGACTGCCCGGTCAA-3' (SEQ ID NO. 23)

12. Stop (3' primer for 3' FTR (truncated stop) and full-length PCR)

5'-CCCGGATCCTACTACATGACTGCCCGGTCAAACAGGTC-3' (SEQ ID NO.24)

---

We claim:

1. A method for making a polypeptide ligand of a target molecule comprising:
 (a) synthesizing a mRNA mixture comprising translatable and nontranslatable regions, wherein said translatable region comprises randomized and fixed sequence coding regions;
 (b) synthesizing a mixture of mRNA·polypeptide copolymers, each member comprising an mRNA and a polypeptide encoded by its associated mRNA, wherein a portion of said nontranslatable region of said mRNA and a portion of said polypeptide encoded by said fixed sequence coding region form a binding interaction;
 (c) partitioning the mRNA·polypeptide copolymers with respect to affinity of the copolymers to a desired target molecule;
 (d) amplifying the mRNA of partitioned copolymers to yield a translatable mRNA mixture; and (e) synthesizing a polypeptide or polypeptides encoded by the mRNA mixture of step (d).

2. The method of claim 1 further comprising the steps of repeating steps (a) through (d) using the mRNA mixture of step (d) in successive cycles repeating as many times as desired to yield copolymers with the desired affinity to the target.

3. The method of claim 1 wherein the target molecule is a protein.

4. The method of claim 3 wherein the protein is an enzyme.

5. The method of claim 3 wherein the protein is an antibody.

6. The method of claim 3 wherein the protein is a receptor.

7. The method of claim 3 wherein the protein is a nucleic acid binding protein.

8. The method of claim 3 wherein the protein is a toxin.

9. The method of claim 3 wherein the protein is a glycoprotein.

10. The method of claim 3 wherein the protein is an antigen.

11. The method of claim 1 wherein the polypeptide is an inhibitor of function of the target molecule.

12. The method of claim 1 wherein the target molecule is a cell membrane component.

13. The method of claim 1 wherein the target molecule is a virus component.

14. The method of claim 1 wherein the target molecule is a carbohydrate.

15. The method of claim 1 wherein the target molecule is a polysaccharide.

16. The method of claim 1 wherein the target molecule is a lipid.

17. The method of claim 1 wherein the target molecule is a glycolipid.

18. The method of claim 1 wherein the target molecule is a toxin.

19. The method of claim 1 wherein the target molecule is a drug.

20. The method of claim 1 wherein the target molecule is a controlled substance.

21. The method of claim 1 wherein the target molecule is a metabolite.

22. The method of claim 1 wherein the target molecule is a cofactor.

23. The method of claim 1 wherein the target molecule is a nucleic acid.

24. The method of claim 1 wherein the target molecule is a hormone.

25. The method of claim 1 wherein the target molecule is a receptor ligand.

26. The method of claim 1 wherein the target molecule is a transition state analog.

27. The method of claim 1 wherein the partitioning is carried out by column chromatography.

28. The method of claim 1 wherein the partitioning is carried out by binding to target molecules attached to a solid phase matrix.

29. The method of claim 1 wherein the partitioning is carried out by immunoprecipitation.

30. The method of claim 1 wherein the partitioning is carried out by indirect immunoprecipitation.

31. The method of claim 1 wherein the mRNA is amplified in step d) by polymerase chain reaction.

32. The method of claim 1 wherein the process of amplifying in step d) includes introducing mutations during amplification.

33. The method of claim 1 wherein step f) is carried out by chemical synthesis of the polypeptide ligand.

34. The method of claim 1 wherein the mRNA additionally comprises a sequence encoding a segment of polypeptide that functions to bind a bridging molecule and step c) further comprises binding target molecules to a solid phase matrix and binding to the target molecules an anchor molecule covalently bound to the bridging molecule, the anchor molecule being capable of specifically binding the target molecules whereby mRNA·polypeptide copolymers bind to the bridging molecule anchored to the target molecules.

35. The method of claim 1 comprising the additional steps of synthesizing a second translatable mRNA mixture comprising the mRNA selected by steps a)–e) and a second randomized sequence coding region, and repeating steps b)–e) using the second translatable mRNA mixture to yield a desired level of target binding by a polypeptide encoded by the second mRNA enriched for sequences encoding the polypeptide.

36. A mixture of mRNA·polypeptide copolymers comprising:
   an mRNA comprising nontranslatable portions and translatable portions;
   a polypeptide encoded by said mRNA comprising random and fixed sequence regions, wherein said mRNA and polypeptide are bound together by at least a portion of the nontranslatable portion of said mRNA and at least a portion of the fixed sequence region of said polypeptide.

37. A method for making a polypeptide ligand of a target molecule comprising:
   (a) synthesizing a mRNA mixture of at least $10^{14}$ sequences comprising translatable and nontranslatable regions;
   (b) synthesizing a mixture of mRNA·polypeptide copolymers, each member comprising an mRNA and a polypeptide encoded by its associated mRNA, and not containing a ribosome;
   (c) partitioning the mRNA·polypeptide copolymers with respect to affinity of the copolymers to a desired target molecule;
   (d) amplifying the mRNA of partitioned copolymers to yield a translatable mRNA mixture; and
   (e) synthesizing a polypeptide or polypeptides encoded by the mRNA mixture of step (d).

38. The method of claim 37 wherein said mRNA·polypeptide copolymers are synthesized by the post-translational or co-translational interaction between a portion of the nontranslatable portion of said mRNA and a portion of said polypeptide.

39. The method of claim 37 wherein said mRNA·polypeptide copolymers are synthesized by crosslinking the polypeptide-tRNA-mRNA complex after translation of the mRNA.

40. The method of claim 37 wherein said mRNA·polypeptide copolymers are synthesized by linking the 5' nucleic acid sequence of the mRNA to the initial amino acid sequences of the polypeptide prior to translation.

* * * * *

UNITED STATES PATENT AND TRADEMARK OFFICE
CERTIFICATE OF CORRECTION

PATENT NO.     : 5,843,701
DATED          : December 1, 1998
INVENTOR(S)    : Larry Gold et al.

It is certified that error appears in the above-identified patent and that said Letters Patent is hereby corrected as shown below:

Column 52,
Line 4, delete "f)" and insert -- e) --.

Signed and Sealed this

Nineteenth Day of July, 2005

JON W. DUDAS
*Director of the United States Patent and Trademark Office*

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:1:

Glu Gln Lys Ile Ser Glu Glu Asp Lys
                  5

( 2 ) INFORMATION FOR SEQ ID NO:2:

( i ) SEQUENCE CHARACTERISTICS:
        ( A ) LENGTH: 50 base pairs
        ( B ) TYPE: nucleic acid
        ( C ) STRANDEDNESS: single ( D ) TOPOLOGY: linear ( x i ) SEQUENCE DESCRIPTION: SEQ ID NO:2:

CCGAAGCTTA ATACGACTCA CTATAGGGCG ACATACATTT ACACACATAA    50

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGGGAATTCT TTCATATTAT ATTTCCTCCT TATGTGTGTA AATGTATG    48

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGCGAATTCT GCTGCTGCAG TGCTGCCATG GTTGCGACGG TCAGGA    46

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCGCCGGATC CTCCTGTCCG TCGCAA    26

( 2 ) INFORMATION FOR SEQ ID NO:6:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CCCGAATTCN NNNNNNNNN NNNNNNNNNN NNNNNNNNNN NNNNNNNNNN    50

NNNNCTGCAG TGCTGCCATG GT    72

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ACCATGGCAG CACTG    15

( 2 ) INFORMATION FOR SEQ ID NO:8:

( i ) SEQUENCE CHARACTERISTICS:
        ( A ) LENGTH: 150 base pairs
        ( B ) TYPE: nucleic acid
        ( C ) STRANDEDNESS: single ( D ) TOPOLOGY: linear ( x i ) SEQUENCE DESCRIPTION: SEQ ID NO:8:

```
GGGCCATGGA CGACGACGAC GACGACGACG ACGACGACGA CGACGACGAC          50
GACGACGACG ACGACGACGA CGACGACGAC GACGACGACG ACGACGACGA         100
CGACGACGAC GACGACGACG ACGACGACGC CATGGTTGCG ATGGTCSGGA         150
```

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
TCCTGTCCAT CGCAA                                                15
```

( 2 ) INFORMATION FOR SEQ ID NO:10:

( i ) SEQUENCE CHARACTERISTICS:
        ( A ) LENGTH: 79 base pairs
        ( B ) TYPE: nucleic acid
        ( C ) STRANDEDNESS: double
        ( D ) TOPOLOGY: linear:

( x i ) SEQUENCE DESCRIPTION: SEQ ID NO:10:

```
CCGAAGCTTA ATACGACTCA CTATAGGGCG ACATACATTT ACACACATAA          50
GGAGGAAAUA UAAUATGAAA GAATTCCCG                                 79
```

( 2 ) INFORMATION FOR SEQ ID NO:11:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
TCGATAAGCT TGATATCGAA TTCCTGCAGC CCGGGGATC CACTAG               46
```

( 2 ) INFORMATION FOR SEQ ID NO:12:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:12:

```
GGCGAATTCT GCTGCTGCAG TGCTGCCATG GTTGCGACGG TCAGGAGGAT CCGGCGG  57
```

( 2 ) INFORMATION FOR SEQ ID NO:13:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
GGGAAGCTTA ATACGACTCA CTATAGGGAG CTTGTTCTTT TTGCAGAAGC          50
TCAG                                                            54
```

( 2 ) INFORMATION FOR SEQ ID NO:14:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

CTCGGCGCTA GCCATGGTGA TCTGCCAAAG TTGAG      3 5

( 2 ) INFORMATION FOR SEQ ID NO:15:

( i ) SEQUENCE CHARACTERISTICS:
    ( A ) LENGTH: 57 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

CCGAAGCTTA ATACGACTCA CTATAGGGTA AGATAAGATA AGGAGGAAAA TAAATGG      5 7

( 2 ) INFORMATION FOR SEQ ID NO:16:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

CTAGCCATTT TATTTTCCTC CTTATCTTAT CTTACCCTAT AGTGAGTCGT      5 0

ATTTAAGCTT CGG      6 3

( 2 ) INFORMATION FOR SEQ ID NO:17:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

GGGCCATGGC TAGCGCCGAG GA      2 2

( 2 ) INFORMATION FOR SEQ ID NO:18:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

GGCGGATCCA GGCGGGACCC TTTCTGCGAC GAA      3 3

( 2 ) INFORMATION FOR SEQ ID NO:19:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

GGGCCATGGC TAGCGCCGAG GAGCAGAAGC TGATCTCCGA GGAGGACCTG      5 0

CTGGAATTCG TCGCAGAAAG GGTCCCG      7 7

( 2 ) INFORMATION FOR SEQ ID NO:20:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

GGGCCATGGC TAGCGCCGAG GAGNNNNNNN NNNNNNNNN NNNNNNCTG    5 0

CTGGAATTCG TCGCAGAAAG GGTCCCG    7 7

( 2 ) INFORMATION FOR SEQ ID NO:21:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

GGGCCATGGC TAGCGCCGAG CTCGAATTCA GCAAAGGTTC GTCGCAGAAA GGGT    5 4

( 2 ) INFORMATION FOR SEQ ID NO:22:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

CCCGGATCCG TGTGTGTGTG TGTGCATGAC TGCCCGGTCA AACAGGTC    4 8

( 2 ) INFORMATION FOR SEQ ID NO:23:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

CCCGGATCCA TGACTGCCCG GTCAA    2 5

( 2 ) INFORMATION FOR SEQ ID NO:24:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

CCCGGATCCT ACTACATGAC TGCCCGGTCA AACAGGTC    3 8